US011555179B2

(12) United States Patent
Boheler et al.

(10) Patent No.: US 11,555,179 B2
(45) Date of Patent: Jan. 17, 2023

(54) IDENTIFICATION OF SUBPOPULATIONS OF CARDIOMYOCYTES

(71) Applicant: The University of Hong Kong, Hong Kong (HK)

(72) Inventors: Kenneth Richard Boheler, Odenton, MD (US); Ngar-Yun Ellen Poon, Lantau Island (HK)

(73) Assignee: THE UNIVERSITY OF HONG KONG, Hong Kong (CN)

( * ) Notice: Subject to any disclaimer, the term of this patent is extended or adjusted under 35 U.S.C. 154(b) by 210 days.

(21) Appl. No.: 16/265,547

(22) Filed: Feb. 1, 2019

(65) Prior Publication Data

US 2020/0248145 A1    Aug. 6, 2020

(51) Int. Cl.
  *C12N 5/077*    (2010.01)
  *G01N 33/569*    (2006.01)
  *G01N 33/50*    (2006.01)

(52) U.S. Cl.
  CPC ....... *C12N 5/0657* (2013.01); *G01N 33/5014* (2013.01); *G01N 33/5061* (2013.01); *G01N 33/56966* (2013.01); *G01N 2333/70596* (2013.01)

(58) Field of Classification Search
  CPC ......... G01N 33/5061; G01N 33/56966; G01N 2333/70596; C12N 5/0657
  See application file for complete search history.

(56) References Cited

U.S. PATENT DOCUMENTS 7,310,147 B2    12/2007    Jiang
9,994,821 B2    6/2018    Keller

FOREIGN PATENT DOCUMENTS

WO    2012/162741    12/2012
WO    2012162741    12/2012

OTHER PUBLICATIONS

Johnson et al. Generation of functional cardiomycotes derived from human somatic cells and therapy for heart diseases. FASEB 31. Suppl. 1, 92-93 (Abstract) (Oct. 2018).*
Mesquita et al. (Investigating Molecular Mechanisms of Type 2 Long QT Syndrome with iPSC-Derived Cardiomyocytes. Circulation. 136 , No. Suppl. 1. Abstract 20475 (Jun. 2018).*
DuBois et al. SIRPA is a specific cell-surface marker for isolating cardiomyocytes derived from human pluripotent cells. Nat Biotechnol. 29 (11): 1011-1018 (Jul. 2018).*
Baillie, et al., "eversible binding of long-chain fatty acids to purified FAT, the adipose CD36 homolog", *J Membr Biol*, 153(1):75-81 (1996).

(Continued)

*Primary Examiner* — Gailene Gabel
(74) *Attorney, Agent, or Firm* — Pabst Patent Group LLP

(57) ABSTRACT

Disclosed are subpopulations of mammalian stem cell- or mammalian progenitor cell-derived cardiomyocytes. The subpopulations of cardiomyocytes contain a portion of a population of mammalian stem cell- or mammalian progenitor cell-derived cardiomyocytes. The subpopulations of cardiomyocytes can be CD36$^+$ subpopulations or CD36$^-$ subpopulations. Disclosed are methods of isolating and of using the subpopulations of cardiomyocytes, particularly in cardiac disease modeling, drug screening, cardiotoxicity testing, and cardiac regeneration/repair.

37 Claims, 14 Drawing Sheets

(56) References Cited

OTHER PUBLICATIONS

Basu, et al., "Purification of specific cell population by fluorescence activated cell sorting (FACS).", *J Vis Exp*, , (41 pii: 1546. doi: 10.3791/1546. (2010).
Bausch-Fluck, et al., "Cell surface capturing technologies for the surfaceome discovery of hepatocytes", *Methods Mol Biol*., 909:1-16 (2012).
Bedada, et al., "Acquisition of a quantitative, stoichiometrically conserved ratiometric marker of maturation status in stem cell-derived cardiac myocytes", *Stem Cell Reports*, 3(4):594-605 (2014).
Bender, et al., "Inhibition of DNA methylation by 5-aza-2'-deoxycytidine suppresses the growth of human tumor cell lines", *Cell*, 58(1):95-101 (1998).
Brandão et al., "Human pluripotent stem cell models of cardiac disease: from mechanisms to therapies", *Dis Model Mech*, 10(9):1039-59 (2017).
Calvo, et al., "Human CD36 is a high affinity receptor for the native lipoproteins HDL, LDL, and VLDL", *J Lipid Res*, 39(4):777-88 (1998).
Chi, "Revolution dawning in cardiotoxicity testing", *Nature Rev Drug Discov*, 12:565-7 (2010).
Da Rocha, et al., "hiPSC-CM Monolayer Maturation State Determines Drug Responsiveness in High Throughput Pro-Arrhythmia Screen", *Sci Rep*, 7(1):13834 (2017).
Dubois, et al., "SIRPA is a specific cell-surface marker for isolating cardiomyocytes derived from human pluripotent stem cells", *Nat Biotechnol*, 29(11):1011-8 (2011).
Endemann, et al., "CD36 is a receptor for oxidized low density lipoprotein", *J Biol Chem*, 268(16):11811-6 (1993).
Friedman, et al., "Single-Cell Transcriptomic Analysis of Cardiac Differentiation from Human PSCs Reveals HOPX-Dependent Cardiomyocyte Maturation", *Cell Stem Cell*, 23(4):586-98 (2018).
Gnecchi, et al., "Paracrine action accounts for marked protection of ischemic heart by Akt-modified mesenchymal stem cells", *Nat Med*, 11:367-8 (2005).
Hoang, et al., "Generation of spatial-patterned early-developing cardiac organoids using human pluripotent stem cells", *Nature Protocols*, 13:723-37 (2018).
Hoof, et al., "Identification of cell surface proteins for antibody-based selection of human embryonic stem cell-derived cardiomyocytes", *J Proteome Res*, 9(3):1610-8 (2010).
Kim and Dyck, "The role of CD36 in the regulation of myocardial lipid metabolism", *Biochim Biophys Acta*, 1860(10):1450-60 (2016).
Kocher, et al., "Neovascularization of ischemic myocardium by human bone-marrow-derived angioblasts prevents cardiomyocyte apoptosis, reduces remodeling and improves cardiac function", *Nat Med*, 7:430-6 (2001).
Lietz, et al., "Outcomes of left ventricular assist device implantation as destination therapy in the post-REMATCH era: implications for patient selection", *Circulation*, 116:497-505 (2007).
Mandenius, et al., "Cardiotoxicity testing using pluripotent stem cell-derived human cardiomyocytes and state-of-the-art bioanalytics: a review", *J Appl Toxicol*, 31(3):191-205 (2012).
Mills, et al., "Functional screening in human cardiac organoids reveals a metabolic mechanism for cardiomyocyte cell cycle arrest.", *PNAS*, 114(40):E8372-E8381 (2017).
Miltenyi, et al., "High gradient magnetic cell separation with MACS", *Cytometry*, 11(2):231-8 (1990).
Modesti, "Fluorescent labeling of proteins", *Methods Mol Biol*, 783:101-20 (2011).
Nicholson, et al., "Oxidized LDL binds to CD36 on human monocyte-derived macrophages and transfected cell lines. Evidence implicating the lipid moiety of the lipoprotein as the binding site", *Arterioscler, Thromb Vasc Biol*,, 15(2):269-75 (1995).

Nugraha, et al., "Human Cardiac Organoids for Disease Modeling",*Clin Pharmacol Ther*, doi: 10.1002/cpt.1286 (2018).
Oettgen, et al., Cardiac Stem Cell Therapy. Need for Optimization of Efficacy and Safety Monitoring *Circulation*, 114:353-8 (2006).
Podrez, et al., "Identification of a novel family of oxidized phospholipids that serve as ligands for the macrophage scavenger receptor CD36", *J Biol Chem*. 277(41):38503-16 (2002).
Poon, et al., "Proteomic Analysis of Human Pluripotent Stem Cell-Derived, Fetal, and Adult Ventricular Cardiomyocytes Reveals Pathways Crucial for Cardiac Metabolism and Maturation", *Circ. Cardiovasc. Genet.*, 8(3):427-36 (2015).
Poon, et al., "Transcriptome-guided functional analyses reveal novel biological properties and regulatory hierarchy of human embryonic stem cell-derived ventricular cardiomyocytes crucial for maturation", *PLoS One*, 8(10):e77784 (2013).).
Rosenstrauch, et al., "Stem celltherapy for ischemic heart failure", *Tex Heart 1st J*, 32:339-47 (2005).
Schuster, et al., "Myocardial neovascularization by bone marrow angioblasts results in cardiomyocyte regeneration", *Am J Physiol Heart Circ Physiol*, 287:H525-H532 (2004).
Shinde, et al., "In Vitro Methods for Cardiotoxicity Testing", *In Vitro Toxicology Systems*, 45-77 (2014).
Silverstein, et al., "Sense and antisense cDNA transfection of CD36 (glycoprotein IV) in melanoma cells. Role of CD36 as a thrombospondin receptor", *J Biol Chem*, 267(23):16607-12 (1992).
Sun, "Cardiotoxicity Testing in drug Development", *Sm J Cardiovasc Dis.*, 1(1):1005 (2016).
Tanaka, et al., "Cardiovascular Disease Modeling Using Patient-Specific Induced Pluripotent Stem Cells", *Int J Mol Sci*, 16(8):18894-922 (2015).
Tandon, et al., "Identification of glycoprotein IV (CD36) as a primary receptor for platelet-collagen adhesion", *J Biol Chem*. 264(13):7576-83 (1989).
Toseland, "Fluorescent Labeling and Modification of Proteins", *J Chem Biol*, 6(3):85-95 (2013).
Uosaki, et al., "Transcriptional Landscape of Cardiomyocyte Maturation", *Cell Reports*, 13(8):1705-16 (2015).
Uosaki, et al., "Efficient and scalable purification of cardiomyocytes from human embryonic and induced pluripotent stem cells by VCAM1 surface expression",*PLoS One*, 6(8):e23657 (2011).
Voges, et al., "Development of a human cardiac organoid injury model reveals innate regenerative potential", *Development*, 144:1118-27 (2017).
Waas, et al., "Are These Cardiomyocytes? Protocol Development Reveals Impact of Sample Preparation on the Accuracy of Identifying Cardiomyocytes by Flow Cytometry", *Stem Cell Reports*, 12(2):395-410 (2019).
Younce, et al., "Hyperglycaemia-induced cardiomyocyte death is mediated via MCP-1 production and induction of a novel zinc-finger protein MCPIP", *Cardiovasc Res*, 87(4):665-74 (2010).
Zhang, et al., "Metformin Protects against H2O2-Induced Cardiomyocyte Injury by Inhibiting the miR-1a-3p/GRP94 Pathway", *Mol Ther: Nucleic Acids*, 13:189-97 (2018).).
Zhao, et al., "Cardiotoxicity evaluation using human embryonic stem cells and induced pluripotent stem cell-derived cardiomyocytes", *Stem Cell Research & Therapy*, 8:54 (2017).
Zhu, et al., "Variability of action potentials within and among cardiac cell clusters derived from human embryonic stem cells", *Sci. Reports*, 6:18544 (2016).
Sun, SM J Cardiovasc Dis., 1(1):1005 (2016).
Uosakio et al., "Efficient and scalable purification of cardiomyocytes from human embryonic and induced pluripotent stem cells by VCAM1 surface expression", PLoS One, 6(8):e23657 (2011).
Zhang, et al., "Metformin Protects against H2O2-Induced Cardiomyocyte Injury by Inhibiting the miR-1a-3p/GRP94 Pathway", Mol Ther: Nucleic Acids, 13:189-97 (2018).).

\* cited by examiner

IDENTIFICATION OF SUBPOPULATIONS OF CARDIOMYOCYTES

FIELD OF THE INVENTION

The disclosed invention is generally in the field of stem cell-derived cardiomyocytes and specifically in the area of identification, isolation and use of subpopulations of stem-cell derived cardiomyocytes.

BACKGROUND OF THE INVENTION

Cardiac muscle cells or cardiomyocytes are the muscle cells (myocytes) that make up the cardiac muscle (heart muscle). Human pluripotent stem cell (hPSC)-derived cardiomyocytes (CMs) are important for the study of human cardiac development, disease modelling, drug screening, and cardiotoxicity testing. However, the in vitro differentiation of hPSCs routinely yields developmentally immature cells with poorly-defined functional properties (Yang, et al., *Circ. Res.*, 2014, 114(3):511-23; Poon, et al., *Circ. Cardiovasc. Genet.*, 2015, 8(3):427-36). It is currently believed that the maturation state of these CMs is "arrested" in an undefined embryonic or fetal stage of development in vitro (Uosaki, et al., *Cell Reports*, 2015, 13(8):1705-16).

Previous maturation strategies focused on altering the phenotype of hPSCs by transgenic approaches, manipulation of signaling pathways, or culture on specific substrates, but functional improvement is often limited. Furthermore, hPSC-derived cardiac cultures consist of CMs with variable proportions and developmental stages of atrial, ventricular, and pacemaker-like cells as well as non-CMs. The use of mixed, immature cultures can adversely affect functional properties and response to stimuli (Zhu, et al., *Scientific Reports*, 2016, 6:18544; da Rocha, et al., *Scientific Reports*, 2017, 7(1):13834; Friedman, et al., *Cell Stem Cell*, 2018, 23(4):586-98 e8).

There is an urgent need for subpopulations of CMs with high homogeneity and uniform functional properties, derived from stem cells, such as totipotent stem cells, pluripotent stem cells, and multipotent stem cells, or from progenitor cells. There is also a tremendous demand for developing methods of identifying and isolating such subpopulations of CMs from stem cell or progenitor cell-derived cardiac cultures.

Therefore, it is the object of the present invention to provide subpopulations of stem cell- or progenitor cell-derived CMs with high homogeneity and uniform functional properties.

It is another object of the present invention to provide methods of identifying and isolating such subpopulations of CMs.

It is yet another object of the present invention to provide methods of using such subpopulations of CMs.

BRIEF SUMMARY OF THE INVENTION

Disclosed are subpopulations of mammalian stem cell- or mammalian progenitor cell-derived cardiomyocytes. The subpopulations of cardiomyocytes contain a portion of a population of mammalian stem cell- or mammalian progenitor cell-derived cardiomyocytes.

The subpopulations of cardiomyocytes can be $CD36^+$ subpopulations or $CD36^-$ subpopulations. The $CD36^+$ subpopulations generally have a higher proportion of cells expressing CD36 on the cell surface than the population of cardiomyocytes had, a higher average expression level of CD36 on the cell surface than the population of cardiomyocytes had, or a combination of both. The $CD36^-$ subpopulations generally have a lower proportion of cells expressing CD36 on the cell surface than the population of cardiomyocytes had, a lower average expression level of CD36 on the cell surface than the population of cardiomyocytes had, or a combination of both.

In some forms, the subpopulations of cardiomyocytes were derived from the population of cardiomyocytes by selecting cells of the population that either (1) express CD36 on the cell surface or (2) do not express CD36 on the cell surface.

In some forms, the subpopulations of cardiomyocytes were derived from the population of cardiomyocytes by selecting cells of the population that either (1) express a relatively higher level of CD36 on the cell surface or (2) express a relatively lower level of CD36 on the cell surface.

In some forms, the population of cardiomyocytes was derived from pluripotent stem cells (such as human pluripotent stem cells). In some forms, the population of cardiomyocytes was derived from embryonic stem cells (such as human embryonic stem cells), or induced pluripotent stem cells (such as human induced pluripotent stem cells). In some forms, the population of cardiomyocytes was derived from totipotent stem cells (such as human totipotent stem cells). In some forms, the population of cardiomyocytes was derived from multipotent stem cells (such as human multipotent stem cells). In some forms, the population of cardiomyocytes was derived from progenitor cells (such as human progenitor cells).

In some forms, the cells in the subpopulations of cardiomyocytes also express one or more markers associated with a cardiac phenotype, such as CD172A (SIRPA), TNNT2, and VCAM1.

Disclosed also are methods for isolating the subpopulations of mammalian stem cell- or mammalian progenitor cell-derived cardiomyocytes. The methods can include: (a) culturing mammalian stem cell- or mammalian progenitor cell-derived cardiomyocytes for a time period sufficient for expression of CD36 on the cell surface of some of the cardiomyocytes; and (b) performing one of the following two procedures: (b1) isolating those of the cardiomyocytes (1) expressing CD36 on the cell surface or (2) not expressing CD36 on the cell surface to yield the subpopulation of cardiomyocytes, or (b2) isolating those of the cardiomyocytes (1) expressing a relatively higher level of CD36 on the cell surface or (2) expressing a relatively lower level of CD36 on the cell surface to yield the subpopulation of cardiomyocytes.

In some forms, step (b1) includes: (i) contacting the cardiomyocytes from step (a) with a sorting agent that is specific for CD36 under conditions sufficient to allow binding of the sorting agent to CD36 on the cell surface of the cardiomyocytes; and
(ii) isolating those of the cardiomyocytes to which the sorting agent (1) has bound or (2) has not bound to yield the subpopulations of cardiomyocytes.

In some forms, step (b2) includes: (i) contacting the cardiomyocytes from step (a) with a sorting agent that is specific for CD36 under conditions sufficient to allow binding of the sorting agent to CD36 on the cell surface of the cardiomyocytes; and
(ii) isolating those of the cardiomyocytes to which the sorting agent (1) has bound at a relatively higher level or (2) has bound at a relatively lower level to yield the subpopulations of cardiomyocytes.

In some forms, the sorting agent can include an antibody specific for CD36. The isolation method in step (b) can be fluorescence-activated cell sorting or magnetic-activated cell sorting.

Disclosed also are methods for using the subpopulations of mammalian stem cell- or mammalian progenitor cell-derived cardiomyocytes, especially the subpopulations of human pluripotent stem cell-derived cardiomyocytes. The subpopulations of cardiomyocytes are applicable to numerous areas including, but not limited to, cardiac disease or disorder modeling, drug screening, cardiotoxicity testing, and cardiac regeneration/repair.

Additional advantages of the disclosed methods and compositions will be set forth in part in the description which follows, and in part will be understood from the description, or can be learned by practice of the disclosed methods and compositions. The advantages of the disclosed methods and compositions will be realized and attained by means of the elements and combinations particularly pointed out in the appended claims. It is understood that both the foregoing general description and the following detailed description are exemplary and explanatory only and are not restrictive of the invention as claimed. It is also understood that the disclosed methods and compositions are not limited to the particular methodology, protocols, and reagents described as these can vary.

BRIEF DESCRIPTION OF THE DRAWINGS

The accompanying drawings, which are incorporated in and constitute a part of this specification, illustrate several embodiments of the disclosed methods and compositions and together with the description, serve to explain the principles of the disclosed methods and compositions.

DETAILED DESCRIPTION OF THE INVENTION

Figure 1A:
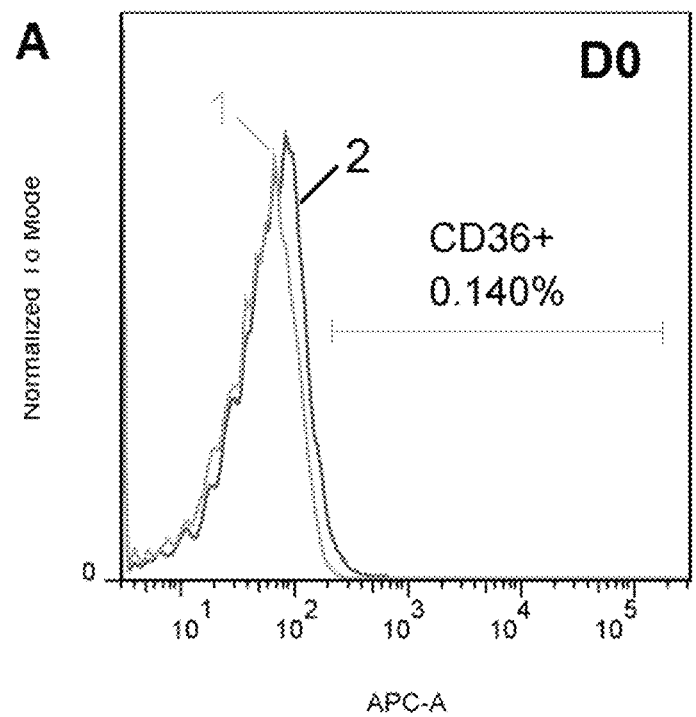
FIGS. 1A-1E are flow cytometry histograms of human embryonic stem cell (hESC)-derived CMs (hESC-CMs) at 0 (A), 15 (B), 30 (C), 45 (D), and 60 (E) days of differentiation. The histograms show the cell counts (normalized to the mode of each peak) plotted against the fluorescence intensity (in a logarithmic scale) of the allophycocyanin (APC) dye. Plots labeled with "1" represent the experimental group in which the cells were stained with an anti-CD36 antibody. Plots labeled with "2" represent the negative control group in which the cells were stained with an isotype antibody. Both the anti-CD36 antibody and the isotype antibody were pre-labeled with APC. The x-axis intervals in which the CD36$^+$ subpopulation of CMs were counted are indicated on the histograms. The amount of the CD36$^+$ subpopulation of CMs is labeled on each histogram as a percentage of the total cell population.
Figure 1B:
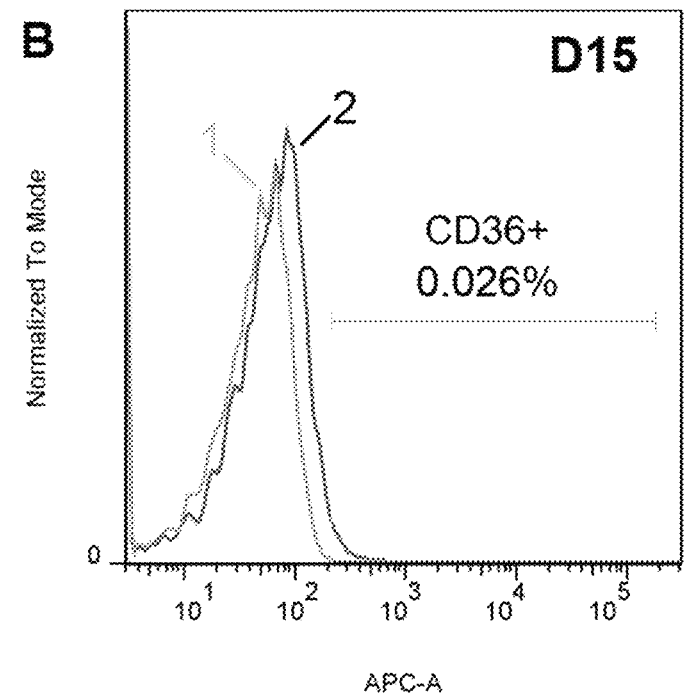
Figure 1C:
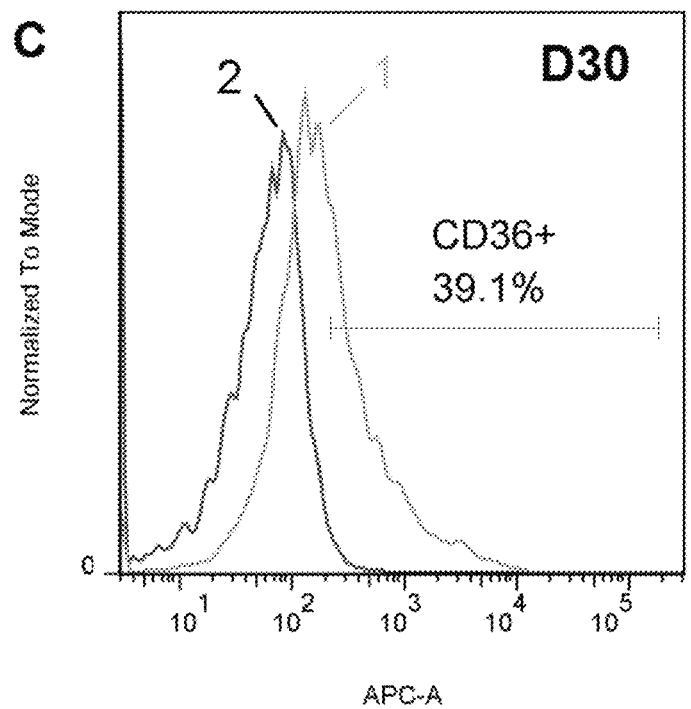

A cell surface marker has been discovered that can identify well-defined and mature cardiomyocytes (CMs) from in vitro differentiated cardiomyocytes. This allows efficient identification and isolation of subpopulations of mature cardiomyocytes (rather than the prior mixtures of mature and immature cardiomyocytes). The discovered cell surface marker is CD36. It is discovered that, consistent with the established role of CD36 as a protein important for metabolism, cardiomyocytes positive for CD36 readily uptake and utilize fatty acids (FAs) as substrates, have a higher content of mitochondria, more polarized $\Delta\psi_m$ and ATP production, and are more sensitive to oxidative stress than cells lacking this surface marker. The methods developed based on this discovery are distinct from and complementary to existing protocols for producing cardiomyocytes, which focus on the manipulation of culture conditions to achieve maturation. The disclosed methods do not require complex and unreliable methods for manipulating cardiomyocytes development. Rather, they depend on identification of the key cell surface marker.

Significantly, isolation of the cardiomyocytes according to the disclosed methods results in a subpopulation of cardiomyocytes with similar levels of CD36, which decreases interline variability and permits a more consistent evaluation of mitochondrial function from diverse PSC lines. It is also discovered that $CD172A^+CD36^+$ cardiomyocytes can be used as a surrogate model of ischemia/perfusion (I/R) and doxorubicin-induced cardiotoxicity. Use of earlier PSC-CMs or unsorted cells leads to less consistent outcomes, likely due to the embryonic-like nature of the cardiomyocytes, which are more tolerant of oxidative stress and thus may not accurately recapitulate the damage response seen in adult patients. Increased sensitivity and more severe damage are demonstrated to more closely mimic the adult phenotype. The use of $CD172^+C6D36^+$ cardiomyocytes subpopulations, with more mature mitochondria and increased sensitivities to oxidative stress, can greatly advance the study of human adult disease phenotypes that involve mitochondrial dysfunction.

The disclosed methods and compositions can be understood more readily by reference to the following detailed description of particular embodiments and the Examples included therein and to the Figures and their previous and following description. All methods described herein can be performed in any suitable order unless otherwise indicated herein or otherwise clearly contradicted by context.

The use of any and all examples or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

The disclosed compositions can be used for, can be used in conjunction with, can be used in preparation for, or are products of the disclosed methods. It is understood that when combinations, subsets, interactions, groups, etc. of these compositions are disclosed, while specific reference of each various individual and collective combinations of these materials may not be explicitly disclosed, each is specifically contemplated and described herein. For example, if a composition is disclosed and discussed and a number of modifications that can be made to a number of compositions including the composition are discussed, each and every combination and permutation of the composition and the modifications that are possible are specifically contemplated unless specifically indicated to the contrary. Thus, if a class of compositions A, B, and C are disclosed as well as a class of compositions D, E, and F and an example of a combinational composition, A-D is disclosed, then even if each is not individually recited, each is individually and collectively contemplated. Thus, in this example, each of the combinations A-E, A-F, B-D, B-E, B-F, C-D, C-E, and C-F are specifically contemplated and should be considered disclosed from disclosure of A, B, and C; D, E, and F; and the example combination A-D. Likewise, any subset or combination of these is also specifically contemplated and disclosed. Thus, for example, the sub-group of A-E, B-F, and C-E are specifically contemplated and should be considered disclosed from disclosure of A, B, and C; D, E, and F; and the example combination A-D. Further, each of the compositions contemplated and disclosed as above can also be specifically and independently included or excluded from any group, subgroup, list, set, etc. of such materials. These concepts apply to all aspects of this application including, but not limited to, steps in methods of making and using the disclosed compositions. Thus, if there are a variety of additional steps that can be performed it is understood that each of these additional steps can be performed with any specific embodiment or combination of embodiments of the disclosed methods, and that each such combination is specifically contemplated and should be considered disclosed.

Throughout the description and claims of this specification, the word "comprise" and variations of the word, such as "comprising" and "comprises," mean "including but not limited to," and are not intended to exclude, for example, other additives, components, integers or steps.

Any discussion of documents, acts, materials, devices, articles or the like which has been included in the present specification is not to be taken as an admission that any or all of these matters form part of the prior art base or were common general knowledge in the field relevant to the present disclosure as it existed before the priority date of each claim of this application.

I. DEFINITIONS

The singular forms "a," "an," and "the" include plural reference unless the context clearly dictates otherwise. For example, reference to "a subpopulation" includes a plurality of subpopulations and reference to "the subpopulation" is a reference to one or more subpopulations and equivalents thereof known to those skilled in the art.

The terms "may," "may be," "can," and "can be," and related terms are intended to convey that the subject matter involved is optional (that is, the subject matter is present in some embodiments and is not present in other embodiments), not a reference to a capability of the subject matter or to a probability, unless the context clearly indicates otherwise.

The terms "optional" and "optionally" mean that the subsequently described event, circumstance, or material may or may not occur or be present, and that the description includes instances where the event, circumstance, or material occurs or is present and instances where it does not occur or is not present.

Use of the term "about" is intended to describe values either above or below the stated value in a range of approx. +/−10%; in other embodiments the values may range in value either above or below the stated value in a range of approx. +/−5%; in other embodiments the values may range in value either above or below the stated value in a range of approx. +/−2%; in other embodiments the values may range in value either above or below the stated value in a range of approx. +/−1%. The preceding ranges are intended to be made clear by context, and no further limitation is implied.

Ranges can be expressed herein as from "about" one particular value, and/or to "about" another particular value.

When such a range is expressed, also specifically contemplated and considered disclosed is the range from the one particular value and/or to the other particular value unless the context specifically indicates otherwise. Similarly, when values are expressed as approximations, by use of the antecedent "about," it will be understood that the particular value forms another, specifically contemplated embodiment that should be considered disclosed unless the context specifically indicates otherwise. It will be further understood that the endpoints of each of the ranges are significant both in relation to the other endpoint, and independently of the other endpoint unless the context specifically indicates otherwise. It should be understood that all of the individual values and sub-ranges of values contained within an explicitly disclosed range are also specifically contemplated and should be considered disclosed unless the context specifically indicates otherwise. Finally, it should be understood that all ranges refer both to the recited range as a range and as a collection of individual numbers from and including the first endpoint to and including the second endpoint. In the latter case, it should be understood that any of the individual numbers can be selected as one form of the quantity, value, or feature to which the range refers. In this way, a range describes a set of numbers or values from and including the first endpoint to and including the second endpoint from which a single member of the set (i.e., a single number) can be selected as the quantity, value, or feature to which the range refers. The foregoing applies regardless of whether in particular cases some or all of these embodiments are explicitly disclosed.

The term "isolated", as used in the context of a subpopulation of cardiomyocytes, indicates that the cells exists apart from their native environment. An isolated cell can be completely separated from other cell types, or be present in an increased amount in a subpopulation.

"Sorting agent" as used herein refers to any compound that can be used to capture a subpopulation of cells bound with the sorting agent from a population of cells. Sorting agent can be a compound, such as a ligand, antibody or aptamer. It is preferred that the interaction between the sorting agent and its target cell is a specific interaction, such as between a target protein on the cell surface and an antibody specific for the target protein. It is to be understood that the term target protein refers to both the overall protein and to portions of the protein, such as an epitope of the protein, that interact specifically with the sorting agent. In some forms, a sorting agent can be used to sort or separate the subpopulation of cells bound with the sorting agent from those that do not. In some forms, the sorting agents are coupled (covalently or non-covalently) to a reporter that can be readily detected and thereby mediate the sorting of cells. Preferably, the reporter is a detection label or tag, such as a fluorescent label, that can mediate sorting. In some forms, the sorting agents are coupled (covalently or non-covalently) onto magnetic beads or magnetic nanoparticles.

"Long-chain fatty acid" refers to fatty acids with an aliphatic tail of 13 to 21 carbons. Long-chain fatty acids include both saturated fatty acid (such as palmitic acid) and unsaturated fatty acid (such as oleic acid).

The terms "high," "higher," "increase," or "elevate" refer to increases above basal levels, e.g., as compared to a control. The terms "low," "lower," or "reduce" refer to decreases below basal levels, e.g., as compared to a control.

The term "monitoring" as used herein refers to any method in the art by which an activity can be measured.

The term "in need of treatment" as used herein refers to a judgment made by a caregiver (e.g., physician, nurse, nurse practitioner, or individual in the case of humans; veterinarian in the case of non-human mammals) that a subject requires or will benefit from treatment. This judgment is made based on a variety of factors that are in the realm of a care giver's expertise, but that include the knowledge that the subject is ill, or will be ill, as the result of a condition that is treatable by the compounds of the invention.

As used herein, "subject" includes, but is not limited to, human or non-human mammals. The term does not denote a particular age or sex. Thus, adult and newborn subjects, as well as fetuses, whether male or female, are intended to be covered. A patient refers to a subject afflicted with a disease or disorder. The term "patient" includes human and non-human mammal subjects.

The term "treatment" or "treating" refers to the medical management of a subject with the intent to cure, ameliorate, stabilize, or prevent a disease, pathological condition, or disorder. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder. It is understood that treatment, while intended to cure, ameliorate, stabilize, or prevent a disease, pathological condition, or disorder, need not actually result in the cure, amelioration, stabilization or prevention. The effects of treatment can be measured or assessed as described herein and as known in the art as is suitable for the disease, pathological condition, or disorder involved. Such measurements and assessments can be made in qualitative and/or quantitative terms. Thus, for example, characteristics or features of a disease, pathological condition, or disorder and/or symptoms of a disease, pathological condition, or disorder can be reduced to any effect or to any amount.

By the term "effective amount" of a composition as provided herein is meant a nontoxic but sufficient amount of the composition to provide the desired result. As will be pointed out below, the exact amount required will vary from subject to subject, depending on the species, age, and general condition of the subject, the severity of the disease that is being treated, the particular compound used, its mode of administration, and the like. Thus, it is not possible to specify an exact "effective amount." However, an appropriate effective amount can be determined by one of ordinary skill in the art using only routine experimentation.

The dosages or amounts of the compositions described herein are large enough to produce the desired effect in the method by which delivery occurs. The dosage should not be so large as to cause adverse side effects, such as unwanted cross-reactions, anaphylactic reactions, and the like. Generally, the dosage will vary with the age, condition, sex and extent of the disease in the subject and can be determined by one of skill in the art. The dosage can be adjusted by the individual physician based on the clinical condition of the subject involved. The dose, schedule of doses and route of administration can be varied.

The efficacy of administration of a particular dose of the compositions according to the methods described herein can be determined by evaluating the particular aspects of the medical history, signs, symptoms, and objective laboratory tests that are known to be useful in evaluating the status of a subject in need for the treatment of cardiac diseases and/or disorders or other diseases and/or conditions. These signs, symptoms, and objective laboratory tests will vary, depending upon the particular disease or condition being treated or prevented, as will be known to any clinician who treats such patients or a researcher conducting experimentation in this field. For example, if, based on a comparison with an appropriate control group and/or knowledge of the normal progression of the disease in the general population or the particular individual: (1) a subject's physical condition is shown to be improved (e.g., the cardiac function is improved), (2) the progression of the disease or condition is shown to be stabilized, or slowed, or reversed, or (3) the need for other medications for treating the disease or condition is lessened or obviated, then a particular treatment regimen will be considered efficacious.

II. MAMMALIAN STEM CELL- OR MAMMALIAN PROGENITOR CELL-DERIVED CARDIOMYOCYTES

The disclosed cardiomyocytes are derived from stem cells, such as totipotent stem cells (TSCs), pluripotent stem cells (PSCs), and multipotent stem cells (MSCs), or from progenitor cells. The TSCs, PSCs, MSCs, and progenitor cells are from human or non-human mammalian sources, such as mouse, rodents, porcine, and non-human primates (e.g., monkey, chimpanzee). The PSCs can be embryotic stem cells (ESCs) or induced pluripotent stem cells (iPSCs). The ESCs can be "true" ESCs derived from embryos, ESCs made by somatic cell nuclear transfer, or ESCs from unfertilized eggs. The MSCs can be from any human or non-human mammalian source and include stem cells variously referred to as adult stem cells, tissue-specific stem cells, and somatic stem cells. As used herein, and unless the context clearly indicates otherwise, reference to a "stem cell" or "stem cells" refers to totipotent, pluripotent, and multipotent stem cells where the cell can be derived from any source (embryo or tissue) and by any means (isolation or induced).

In some forms, the cardiomyocytes are derived from human ESCs (hESCs), such as the hESC cell lines listed in the NIH Human Embryonic Stem Cell Registry (internet site grants.nih.gov/stem_cells/registry/current.htm). In some forms, the cardiomyocytes are derived from hESC Line H7 or H9.

In some forms, the cardiomyocytes are derived from human iPSCs (hiPSCs). In some forms, the cardiomyocytes are derived from MD1-hiPSCs.

In some forms, the cardiomyocytes express one or more markers associated with a cardiac phenotype, such as CD172A (SIRPA), TNNT2, and VCAM1. Additional markers specific for cardiomyocytes can be found in PCT Patent Application No. WO 2015/172037 and U.S. Patent Application Publication No. US 2017/0349883. The population of cardiomyocytes can be isolated from the stem cell- or progenitor cell-derived cardiomyocyte cell culture by selecting cells that express one or more markers associated with a cardiac phenotype, e.g., CD172A and VCAM1. This process ensures that no other types of cells are present in the population of cardiomyocytes.

Methods of generating stem cell- or progenitor cell-derived cardiomyocytes, especially hPSC-derived cardiomyocytes, are known to one of ordinary skill in the art. See, for example, Brandão, et al., *Dis Model Mech*, 2017, 10(9): 1039-1059; Yang, et al., *Nature*, 2008, 453:524-528; and Laflamme, et al., *Nat Biotechnol*, 2007, 25:1015-1024.

III. SUBPOPULATIONS OF CARDIOMYOCYTES

CD36 encodes a fatty acid translocase which is upregulated during cardiac development, and is only present in a subset of in vitro differentiated cardiomyocytes.

Disclosed are subpopulations of mammalian stem cell- or mammalian progenitor cell-derived cardiomyocytes, wherein the subpopulations of cardiomyocytes contain a portion of a population of mammalian stem cell- or mammalian progenitor cell-derived cardiomyocytes. The subpopulations of cardiomyocytes can be $CD36^+$ subpopulations or $CD36^-$ subpopulations. The $CD36^+$ subpopulations have a higher proportion of cells expressing CD36 on the cell surface than the population of cardiomyocytes had, a higher average expression level of CD36 on the cell surface than the population of cardiomyocytes had, or a combination of both. The $CD36^-$ subpopulations have a lower proportion of cells expressing CD36 on the cell surface than the population of cardiomyocytes had, a lower average expression level of CD36 on the cell surface than the population of cardiomyocytes had, or a combination of both.

In some forms, the subpopulations of cardiomyocytes were derived from the population of cardiomyocytes by selecting cells of the population that either (1) express CD36 on the cell surface or (2) do not express CD36 on the cell surface.

In some forms, the subpopulations of cardiomyocytes were derived from the population of cardiomyocytes by selecting cells of the population that either (1) express a relatively higher level of CD36 on the cell surface or (2) express a relatively lower level of CD36 on the cell surface.

Isolation of stem cell- or progenitor cell-derived cardiomyocytes with similar levels of CD36 decreases interline variability and permits a more consistent evaluation of mitochondrial function of cardiomyocytes derived from diverse mammalian stem cell or progenitor cell lines.

In some forms, the cells of the subpopulations of cardiomyocytes express one or more markers associated with a cardiac phenotype, such as CD172A (SIRPA), TNNT2, and VCAM1. Any one or more of such markers can be used to define a population of cells from which the disclosed subpopulations of cardiomyocytes are isolated or derived.

1. $CD36^+$ Subpopulations

In some forms, the subpopulation of cardiomyocytes has a higher proportion of cells expressing CD36 on the cell surface than the population of cardiomyocytes had, a higher average expression level of CD36 on the cell surface than the population of cardiomyocytes had, or a combination of both ($CD36^+$ subpopulation of cardiomyocytes).

In some forms, the proportion of cells of the $CD36^+$ subpopulation expressing CD36 on the cell surface can be different than the proportion of cells of the population of cardiomyocytes expressing CD36 on the cell surface by a factor of between about 1.5 and about 10, between about 1.5 and about 5, between about 1.5 and about 3. The factor is calculated as the ratio of the proportion of cells of the $CD36^+$ subpopulation expressing CD36 on the cell surface to the proportion of cells of the population of cardiomyocytes expressing CD36 on the cell surface.

In some forms, more than 80% of cells in the CD36$^+$ subpopulation express CD36 on the cell surface. Preferably, more than 90% cells in the CD36$^+$ subpopulation express CD36 on the cell surface. Most preferably, more than 95% cells in the CD36$^+$ subpopulation express CD36 on the cell surface.

In some forms, the average expression level of CD36 on the cell surface of the CD36$^+$ subpopulation is between about 1.5-fold and about 200-fold higher than that for the population of cardiomyocytes. Preferably, the average expression level of CD36 on the cell surface of the CD36$^+$ subpopulation is between about 2-fold and about 100-fold higher than that for the population of cardiomyocytes. More preferably, the average expression level of CD36 on the cell surface of the CD36$^+$ subpopulation is between about 2-fold and about 20-fold higher than that for the population of cardiomyocytes.

The average expression level of CD36 on the cell surface can be determined using CD36 staining, which can include the use of an anti-CD36 antibody coupled with a fluorescence dye. In some forms, the signal intensity of CD36 staining for the CD36$^+$ subpopulation is between about 1.5-fold and about 200-fold higher than that for the population of cardiomyocytes. Preferably, the intensity of CD36 staining for the CD36$^+$ subpopulation is between about 2-fold and about 100-fold higher than that for the population of cardiomyocytes. More preferably, the intensity of CD36 staining for the CD36$^+$ subpopulation is between about 2-fold and about 20-fold higher than that for the population of cardiomyocytes.

In some forms, cells in the CD36$^+$ subpopulation have an increased maturation status compared to the CD36$^-$ subpopulation from the same population of cardiomyocytes. For example, cells in the CD36$^+$ subpopulation have a lower spontaneous beating frequency, a higher proportion of binucleated cells, higher expression of one or more sarcomeric proteins involved in cardiac maturation (such as TNNI3, MYL2, or a combination thereof), higher expression of one or more ion channels involved in cardiac maturation (such as KCNJ2), lower expression of one or more extracellular matrix proteins (such as COL8A1), lower expression of one or more cell adhesion proteins (such as NRP2), higher expression of one or more genes involved in mitochondrial function (such as ATP5G4, ACADM, or a combination thereof), higher expression of one or more centromeric genes (such as CENPH, CENPM, or a combination thereof), higher expression of one or more genes associated with DNA repair (such as EXO1, CDK1, or a combination thereof), higher mitochondrial content, more polarized mitochondrial membrane potential, higher ATP production, higher cellular uptake of fatty acids (such as long-chain fatty acids, e.g., oleic acid and palmitic acid), a larger increase in mitochondrial membrane potential when fed with long-chain fatty acids, or combinations thereof, as compared to the CD36$^-$ subpopulation from the same population of cardiomyocytes. In some forms, the fold difference (upregulation or downregulation) for one or more of the aforementioned gene/protein expression levels between the CD36$^+$ subpopulation and the CD36$^-$ subpopulation is at or above 1.2, more preferably at or above 1.4.

The CD36$^+$ subpopulation of cardiomyocytes has a more adult-like metabolic phenotype and displays more mature mitochondria with increased sensitivities to oxidative stress, whereas the CD36$^-$ subpopulation is more hypoxia resistant.

2. CD$^-$ Subpopulations

In some forms, the subpopulation of cardiomyocytes have a lower proportion of cells expressing CD36 on the cell surface than the population of cardiomyocytes had, a lower average expression level of CD36 on the cell surface than the population of cardiomyocytes had, or a combination of both (CD36$^-$ subpopulation of cardiomyocytes).

The proportions of cells of the CD36$^-$ subpopulation not expressing CD36 on the cell surface can be different than the proportion of cells of the population of cardiomyocytes not expressing CD36 on the cell surface by a factor of between about 1.5 and about 10, between about 1.5 and about 5, between about 1.5 and about 3. The factor is calculated as the ratio of the proportion of cells of the CD36$^-$ subpopulation not expressing CD36 on the cell surface to the proportion of cells of the population of cardiomyocytes not expressing CD36 on the cell surface.

In some forms, more than 80% of cells in the CD36$^-$ subpopulation do not express CD36 on the cell surface. Preferably, more than 90% cells in the CD36$^-$ subpopulation do not express CD36 on the cell surface. Most preferably, more than 95% cells in the CD36$^-$ subpopulation do not express CD36 on the cell surface.

In some forms, the average expression level of CD36 on the cell surface of the CD36$^-$ subpopulation is lower than that for the population of cardiomyocytes. Preferably, the average expression level of CD36 on the cell surface of the CD36$^-$ subpopulation is more than 2-fold lower than that for the population of cardiomyocytes.

The average expression level of CD36 on the cell surface can be determined using CD36 staining, which can include the use of an anti-CD36 antibody coupled with a fluorescence dye. In some forms, the signal intensity of CD36 staining for the CD36$^-$ subpopulation is lower than that for the population of cardiomyocytes. Preferably, the intensity of CD36 staining for the CD36$^-$ subpopulation is more than 2-fold lower than that for the population of cardiomyocytes.

In some forms, cells in the CD36$^-$ subpopulation have a decreased maturation status compared to the CD36$^+$ subpopulation from the same population of cardiomyocytes. For example, cells in the CD36$^-$ subpopulation have a higher spontaneous beating frequency, a lower proportion of binucleated cells, lower expression of one or more sarcomeric proteins involved in cardiac maturation (such as TNNI3, MYL2, or a combination thereof), lower expression of one or more ion channels involved in cardiac maturation (such as KCNJ2), higher expression of one or more extracellular matrix proteins (such as COL8A1), higher expression of one or more cell adhesion proteins (such as NRP2), lower expression of one or more genes involved in mitochondrial function (such as ATP5G4, ACADM, or a combination thereof), lower expression of one or more centromeric genes (such as CENPH, CENPM, or a combination thereof), lower expression of one or more genes associated with DNA repair (such as EXO1, CDK1, or a combination thereof), lower mitochondrial content, less polarized mitochondrial membrane potential, lower ATP production, lower cellular uptake of fatty acids (such as long-chain fatty acid, e.g., oleic acid and palmitic acid), a smaller increase in mitochondrial membrane potential when fed with long-chain fatty acids, or combinations thereof, as compared to the CD36$^+$ subpopulation from the same population of cardiomyocytes. In some forms, the fold difference (upregulation or downregulation) for one or more of the aforementioned gene/protein expression levels between the CD36$^+$ subpopulation and the CD36$^-$ subpopulation is at or above 1.2, more preferably at or above 1.4.

IV. ISOLATING THE SUBPOPULATIONS OF CARDIOMYOCYTES

Methods of isolating the subpopulations of mammalian stem cell- or mammalian progenitor cell-derived cardiomyocytes are disclosed. In some forms, the methods include (a) culturing mammalian stem cell- or mammalian progenitor cell-derived cardiomyocytes for a time period sufficient for expression of CD36 on the cell surface of some of the cardiomyocytes; and (b) performing one of the following two procedures: (b1) isolating those of the cardiomyocytes (1) expressing CD36 on the cell surface or (2) not expressing CD36 on the cell surface to yield the subpopulation of cardiomyocytes, or (b2) isolating those of the cardiomyocytes (1) expressing a relatively higher level of CD36 on the cell surface or (2) expressing a relatively lower level of CD36 on the cell surface to yield the subpopulation of cardiomyocytes.

In some forms, the time period in step (a) is between about 2 and about 150 days, between about 10 and about 120 days, between about 15 and about 90 days, or between about 30 and about 60 days, as demonstrated in the Examples.

The methods can include an additional step before step (b): detecting the average expression level of CD36 on the cell surface of the cardiomyocytes. Expression of CD36 on the cell surface can be identified using techniques known to one of ordinary skill in the art, such as flow cytometry, immunohistochemistry, ELISA, or fluorescence imaging.

1. Methods of Isolation

Methods of isolating cells expressing a protein of interest are known to one of ordinary skill in the art. See, for example, U.S. Pat. No. 9,994,821 by Keller, et al; Hoof, et al., *J Proteome Res*, 2010, 9(3):1610-1618.

In some forms, step (b1) includes: (i) contacting the cardiomyocytes from step (a) with a sorting agent that is specific for CD36 under conditions sufficient to allow binding of the sorting agent to CD36 on the cell surface of the cardiomyocytes; and (ii) isolating those of the cardiomyocytes to which the sorting agent (1) has bound or (2) has not bound to yield the subpopulations of cardiomyocytes.

In some forms, step (b2) includes: (i) contacting the cardiomyocytes from step (a) with a sorting agent that is specific for CD36 under conditions sufficient to allow binding of the sorting agent to CD36 on the cell surface of the cardiomyocytes; and (ii) isolating those of the cardiomyocytes to which the sorting agent (1) has bound at a relatively higher level or (2) has bound at a relatively lower level to yield the subpopulations of cardiomyocytes.

In some forms, the sorting agent is an antibody specific for CD36 (anti-CD36 antibody), an anti-CD36 antibody fragment, or a protein comprising an antibody variable region. Exemplary antibodies are chimeric antibodies, humanized antibodies, or human antibodies. The antibody can be polyclonal or monoclonal. Polyclonal and monoclonal antibodies of CD36 can be obtained commercially or produced using well established methods. For example, Johnstone and Thorpe, Immunochemistry in Practice, 1996, 3rd Edition, Blackwell Scientific Pub., London; Harlow and Lane, Antibodies: A Laboratory Manual, 1988, Cold Spring Harbor Laboratory, Cold Spring Harbor, N.Y. Exemplary anti-CD36 antibodies are commercially available, such as the polyclonal CD36 antibody from ThermoFisher Scientific (catalog #: PA1-16813; RRID: AB_568487), the polyclonal CD36 antibody from Abcam (ab124515), the monoclonal CD36 antibody from BioLegend (catalog #: 102605 & 102606; RRID: AB_389348 & AB_389349). In some forms, the anti-CD36 antibody is APC Mouse Anti-Human CD36 Clone CB38 (also known as NL07) from BD Biosciences (catalog No. 550956).

In some forms, the sorting agent is a substrate or substrate analog for CD36, including fatty acids such as long-chain fatty acids, e.g., oleic acid and palmitic acid. The accumulation and levels of the substrates or substrate analogs can correlate with the CD36 levels.

In some forms, the sorting agent is a ligand for CD36. The ligands for CD36 include, but are not limited to, collagens (Tandon, et al., *Journal of Biological Chemistry*, 1989, 264(13):7576-83), thrombospondins (Silverstein, et al., *Journal of Biological Chemistry*, 1992, 267(23):16607-12), erythrocytes parasitized with *Plasmodium falciparum* (Oquendo, et al., *Cell*, 1989, 58(1):95-101), oxidized lipoproteins (Endemann, et al., *Journal of Biological Chemistry*, 1993, 268(16):11811-6; Nicholson, et al., *Arteriosclerosis, Thrombosis, and Vascular Biology*, 1995, 15(2):269-75), native lipoproteins (Calvo, et al., *Journal of Lipid Research*, 1998, 39(4):777-88), oxidized phospholipids (Podrez, et al., *Journal of Biological Chemistry*, 2002, 277(41):38503-16), and long-chain fatty acids (Baillie, et al., *Journal of Membrane Biology*, 1996, 153(1):75-81).

In some forms, the sorting agent is covalently or noncovalently labeled with a detection label. A variety of detection labels are known to the skilled artisan, as are methods for conjugating the detection labels to the sorting agent. See, for example, Modesti, Fluorescent Ladling of Proteins, *Methods Mol Biol*, 2011; 783:101-20; Toseland, Fluorescent Labeling and Modification of Proteins, *J Chem Biol*, 2013, 6(3):85-95. Representative detection labels include, but are not limited to, chromophores, fluorophores, enzymes, antigens, chemiluminescent moieties, electrochemically detectable moieties, etc. In some forms, the sorting agent is biotinylated. In some forms, the biotinylated sorting agent (the first sorting agent) which bind to CD36 on the cell surface are detected using a second sorting agent containing an avidin or streptavidin group that is conjugated to a fluorescent label (e.g., Cy3, Cy5, and Cy7). In some forms, the sorting agent is labeled with a fluorescent label such as a cyanine dye (e.g., Cy3, Cy5, and Cy7), for direct detection.

In some forms, the sorting agent is attached (either covalently or noncovalently) to magnetic beads. In some forms, the sorting agent is attached (either covalently or noncovalently) to magnetic nanoparticles.

In some forms, in step (b) the subpopulation of cardiomyocytes is isolated using fluorescence-activated cell sorting. Methods for fluorescence-activated cell sorting are known to a skilled person in the art. See, for example, Basu, et al., *J Vis Exp*, 2010, (41):1546. In some forms, the sorting agents can be directly labeled with a fluorescent label; in some forms, the sorting agent is an anti-CD36 antibody directly labeled with a fluorescent label.

In some forms, in step (b) the subpopulation of cardiomyocytes is isolated using magnetic-activated cell sorting. Methods for magnetic-activated cell sorting are known to a skilled person in the art. See, for example, PCT Patent Application No. WO 2012/162741 by Elliott, et al.; Uosaki, et al., *PLoS One*, 2011, 6(8):e23657; Miltenyi, et al., *Cytometry*, 1990, 11(2):231-238. In some forms, the sorting agent can be directly attached to magnetic nanoparticles; in some forms, the sorting agent is an anti-CD36 antibody directly attached to magnetic nanoparticles. In some forms, the sorting agent can be directly attached to magnetic beads; in some forms, the sorting agent is an anti-CD36 antibody directly attached to magnetic beads.

In some forms, in step (b) the subpopulation of cardiomyocytes is isolated by chromatography, such as affinity chromatography.

In some forms, in step (b) the subpopulation of cardiomyocytes is isolated by microchips. In some forms, a tiny sample containing unsorted cardiomyocytes is injected into a microfabricated chip containing microfluidic channels. The sample fluid moves through the tiny channels, pneumatically controlled by pumps and valves. Cells pass single-file through a laser in a sorting area, and the scattered and fluorescent light signals are collected. Pumps can re-route the direction of travel for individual cells, for example to send them to a "waste" channel or a "keep" channel. Alternatively, it can send them back into the sorting line to be analyzed again for verification.

Other methods for isolating cells expressing a protein of interest for further propagation can also be used to isolate the subpopulations of cardiomyocytes. For example, cardiomyocytes expressing CD36 or having a relatively higher expression level of CD36 can be isolated using the commercially available ClonePix FL system (Gentix, UK) as disclosed in U.S. Pat. No. 7,310,147, which works by imaging thousands of single cell-derived colonies. Specific fluorescent probes are used to detect and identify colonies that express the highest level of CD36. These colonies are then automatically collected.

2. Additional Procedures/Steps

In some forms, the disclosed methods further include an additional step of isolating cardiomyocytes that express one or more markers associated with a cardiac phenotype, such as CD172A, TNNT2, and VCAM1. This additional step can be performed after step (a) to ensure that no other cell types are present in the population of cardiomyocytes. For example, cells expressing a cardiac marker of interest can be isolated using the commercially available ClonePix FL system (Gentix, UK) as described above. Successive passage of isolated clusters of the colonies with high expression levels of the cardiac marker results in a purer population of cardiomyocytes. In other forms, a cell surface cardiac marker, such as CD172A and VCAM1, can be employed to isolate cardiomyocytes, using methods involving a sorting agent specific for the cell surface cardiac marker, as described above.

The additional step of isolating cardiomyocytes that express one or more markers associated with a cardiac phenotype can be performed before, together with, or after sorting the cardiomyocytes based on the expression of CD36 on the cell surface.

In some forms, the additional step include after step (a): (i) contacting the cardiomyocyte cell culture with a sorting agent, such as an antibody, that is specific for CD172A under conditions sufficient to allow binding of the sorting agent to CD172A; (ii) isolating cells to which the sorting agent has bound.

V. USES OF CD36 AS A MARKER FOR MATURATION

The application of stem cell- or progenitor cell-derived CMs for disease modeling and drug screening may require that they recapitulate the adult cardiac phenotype. However, in vitro differentiation of stem cells, such as TSCs and PSCs, or of progenitor cells routinely yields immature cells with poorly-defined functional properties. The use of such mixed, immature cultures can adversely affect functional properties and response to stimuli. Quantitative assessment of the maturation status of stem cell- or progenitor cell-derived CMs is of paramount importance to ensure functionality and consistency. For example, hPSC-CM cultures are routinely screened for cardiac markers such as cardiac troponin T (Poon, et al., *PLoS One*, 2013, 8(10):e77784) and CD172/SIRPA (Dubois, et al., *Nat Biotechnol*, 2011, 29(11):1011-8) by flow cytometry to ensure that they contain an adequate proportion of CMs, but maturation markers are limited.

Bedada et al. proposed that the use of cardiac troponin I (cTnI)/slow skeletal troponin I isoforms may inform structural maturation (Bedada, et al., Stem *Cell Reports*, 2014, 3(4):594-605), but the detection of cardiac troponin I by flow cytometry can be greatly affected by the antibodies and staining conditions used (Waas, et al., *Stem Cell Reports*, 2019). More importantly, unlike work presented by Bedada et al., cTnI is detected in CMs early in differentiation (around Day 25 of maturation), and thus may not be suitable as a marker of maturation.

CD36 can be used as part of a quality control protocol to ascertain the state of metabolic maturation of cardiomyocytes, including live cardiomyocytes. The level of CD36 expression on the cell surface of cardiomyocytes, such as stem cell- or progenitor cell-derived cardiomyocytes, can be determined using techniques known to one of ordinary skill in the art, such as flow cytometry, immunohistochemistry, ELISA, or fluorescence imaging. A higher expression level of CD36 on the cell surface can correspond to a more metabolic maturation state of the cardiomyocytes. The procedure can also include performing parallel measurement on negative and/or positive control samples. The negative control samples include undifferentiated stem cells or undifferentiated progenitor cells from the same source, immature stem cell- or immature progenitor cell-derived cardiomyocytes from the same source, etc. The positive control samples include mature stem cell- or mature progenitor cell-derived cardiomyocytes from the same source.

In some forms, the cardiomyocytes under examination are derived from mammalian stem cells or mammalian progenitor cells, such as human stem cells or human progenitor cells.

VI. USES OF THE SUBPOPULATION OF CARDIOMYOCYTES

The disclosed subpopulations of cardiomyocytes are applicable to numerous areas including, but not limited to cardiac disease or disorder modeling, drug screening, cardiotoxicity testing, and cardiac regeneration. Other uses include study of cardiac development. Preferably, the subpopulations of hPSC-derived cardiomyocytes are used in these applications.

In some forms, the subpopulations of cardiomyocytes can be used to generate cardiac organoids using methods known to a skilled artisan. See, for example, Nugraha, et al., *Clin Pharmacol Ther*, 2018, doi: 10.1002/cpt.1286; Mills, et al., *PNAS*, 2017, 114(40):E8372-E8381; Hoang, et al., *Nature Protocols*, 2018, 13:723-737; Voges, et al., *Development*, 2017, 144:1118-1127; and references cited therein. The cardiac organoids can be used in the aforementioned applications as well.

1. Disease Modeling, Drug Screening, and Cardiotoxicity Testing

The disclosed subpopulations of cardiomyocytes or the corresponding cardiac organoids can be used for cardiac disease or disorder modeling, drug screening, and cardiotoxicity testing. The CD36$^+$ subpopulations can be used as a phenotype for adult/mature cardiomyocytes; the CD36$^-$ subpopulations can be used as a phenotype for immature cardiomyocytes.

The subpopulations of cardiomyocytes can be used to model a wide array of cardiac diseases and disorders, including but not limited to, primary arrhythmic diseases such as cardiac arrhythmia, cardiomyopathies, cardiometabolic diseases, mitochondrial disorders, endoplasmic reticulum disorders, diabetic cardiomyopathy, and ischemia/reperfusion.

In some forms, the cardiac disease or disorder is induced by doxorubicin-induced cardiotoxicity, long QT syndrome, Brugada syndrome, genetic heart disease, amyloidosis, progeria, diabetic coma, jellyfish intoxication, hyperthyroidism, Yellow Fever, Chagas disease, aortic valve regurgitation, prescription drug abuse leading to arrhythmia, Rett syndrome, myocarditis, tricuspid atresia, Lyme disease, Churg-Strauss syndrome, forms of heart disease or failure involving arrhythmia, enlarged heart, broken heart syndrome, thyroid nodules, atrioventricular canal defect, cholera, mitral valve stenosis, multiple system atrophy (MSA), snoring, mitral valve prolapse, amniotic fluid embolism, gangrene, aplastic anemia, congenital heart disease in adults, heat exhaustion, Graves' disease, cardiomyopathy, premature ventricular contractions, Bradycardia, fatigue, tachycardia, dizziness or shortness of breath, diabetes, arrhythmogenic right ventricular cardiomyopathy, dilated or hypertrophic cardiomyopathies, or muscular dystrophies including but not limited to Duchenne and Becker muscular dystrophies and mitochondrial diseases.

The general procedures of disease modeling can include (a) inducing a cardiac disease or disorder in the subpopulation of cardiomyocytes or the cardiac organoid derived therefrom, using a chemical approach or a biological approach; (b) characterizing the cardiac disease or disorder in the subpopulation of cardiomyocytes or the cardiac organoid from step (a); and optionally (c) evaluating the efficacy of a cardiac drug or therapy. Alternatively, the procedures can include (a) inducing a cardiac disease or disorder in a population of cardiomyocytes; (b) sorting the cells to obtain the subpopulation of cardiomyocytes; (c) characterizing the disease or disorder in the subpopulation of cardiomyocytes from step (b); and optionally (d) evaluating the efficacy of a cardiac drug or therapy.

In some forms, the chemical approach includes exposing the cardiomyocytes or the cardiac organoids derived therefrom to a specific chemical environment to induce a disease state. For example, the cardiomyocytes can be exposed to hydrogen peroxide or low oxygen levels (hypoxia) to mimic oxidative stress-induced cardiomyocyte apoptosis, as frequently encountered in ischemia/reperfusion injuries (Zhang, et al., *Molecular Therapy: Nucleic Acids*, 2018, 13:189-197). For another example, the cardiomyocytes can be exposed to a high concentration of glucose to mimic hyperglycaemia-induced cardiomyocyte damage (Younce, et al., *Cardiovascular Research*, 2010, 87(4):665-674).

In some forms, the biological approach includes genetic modifications on the starting cells, e.g., stem cells or progenitor cells, or the differentiated product, e.g., stem cell- or progenitor cell-derived CMs, to induce one or more genetic defects or mutations. For example, mutation of long QT syndrome (LQTS)-associated genes, such as LQT1 and LQT2, can produce cardiomyocytes as models for primary arrhythmic diseases (Brandão, et al., *Dis Model Mech*, 2017, 10(9):1039-1059).

In some forms, iPSCs such as hiPSCs can be generated from patients with the cardiac disease or disorder via reprogramming, and cardiomyocytes can then be differentiated from these "disease" iPSCs. The CD36$^+$ or CD36$^-$ subpopulations derived thereof can recapitulate the patient's phenotype for studies of disease mechanism or evaluation of potential therapy.

Characterizing the disease state or evaluating the efficacy of therapies can be achieved by monitoring the physical and biological properties of the subpopulations of cardiomyocytes and accessing the changes caused by either the induction of the disease state or the onset of therapies. In some forms, monitoring the physical and biological properties of the subpopulations of cardiomyocytes can be performed using one or more of the following measurement approaches: electrophysiology measurement such as patch clamp and microelectrode arrays, optical measurement such as fluorescence imaging, contraction force measurement, and mitochondrial function measurement. In some forms, the optical measurement is performed using fluorescence dyes specific for different biomolecules, such as calcium dyes (e.g., Fluo-4 AM, Rhod-2 AM) and mitochondrial dyes (e.g., MitoTracker™ green for mitochondrial mass, MitoSOX™ red dye for mitochondrial superoxide), as well as fluorescence dyes indicative of the metabolic, physiological, energy, or viability state of cells, such as tetramethylrhodamine ethyl ester for mitochondrial membrane potential, CellTiter-Glo® luminescent assay for cell viability or ATP production, Hoechst staining for nuclear condensation, PrestoBlue® staining for cell viability, and XTT for cell viability. Mitochondrial function measurements can include metabolic flux assays such as the Seahorse metabolic assays and metabolomics assays.

Drug screening and cardiotoxicity testing can be performed using methods as described above. In some forms, the general procedures for screening drugs or therapies for a cardiac disease or disorder can include (a) inducing the cardiac disease or disorder in the subpopulation of cardiomyocytes or the cardiac organoid derived therefrom, using a chemical approach or a biological approach; (b) treating the subpopulation of cardiomyocytes or the cardiac organoid from step (a) with an effective amount of one or more candidate compounds or therapies; and (c) evaluating the efficacy of the candidate compound or therapy in reducing one or more symptoms of the cardiac disease or disorder.

In some forms, cardiotoxicity testing can be performed by measuring the cellular changes of the subpopulations of cardiomyocytes induced by one or more toxic or potentially toxic stimuli, such as a chemical compound (e.g., a drug such as a cardiac drug or anti-cancer drug). In some forms, the chemical compound is doxorubicin. In some forms, cardiotoxicity testing can include (a) contacting the compound with the subpopulation of cardiomyocytes; and (b) measuring the cardiotoxic effect of the compound on the subpopulation of cardiomyocytes. The cardiotoxic effect of the compound can be determined by monitoring the physical and biological properties of the subpopulations of cardiomyocytes and assessing the changes caused by the compound.

Additional methods for cardiac disease or disorder modeling, drug screening, and cardiotoxicity testing can be found in the following references and references cited therein: Brandão, et al., *Dis Model Mech*, 2017, 10(9):1039-1059; Tanaka, et al., *Int J Mol Sci*, 2015, 16(8):18894-18922; Mandenius, et al., *J Appl Toxicol*, 2011, 31(3):191-205; Sun, *SM J Cardiovasc Dis*, 2016, 1(1):1005; Chi, *Nature Reviews Drug Discovery*, 2013, 12:565-567; Shinde, et al., In Vitro Methods for Cardiotoxicity Testing, in *In Vitro Toxicology Systems*, 2014, 45-77; and Zhao, et al., *Stem Cell Research & Therapy*, 2017, 8:54.

2. Cardiac Regeneration and Repair

The disclosed subpopulations of cardiomyocytes can also be used for treating one or more cardiac diseases or disorders such as heart failure and/or improve heart function through cardiac regeneration or repair.

Ischemic heart failure occurs when cardiac tissue is deprived of oxygen and blood flow is at abnormally low levels. When the ischemic insult is severe enough to cause the loss of critical amounts of cardiomyocytes, this loss initiates a cascade of detrimental events, including formation of a non-contractile scar, ventricular wall thinning, an overload of blood flow and pressure, ventricular remodeling (the overstretching of viable cardiac cells to sustain cardiac output), heart failure, and eventual death (Rosenstrauch, *Tex Heart 1st J*, 2005, 32:339-347). Restoring damaged heart muscle tissue, through repair or regeneration, therefore represents a fundamental mechanistic strategy to treat heart failure. Current pharmacologic interventions for heart disease, including beta-blockers, diuretics, and angiotensin-converting enzyme (ACE) inhibitors, and surgical treatment options, such as changing the shape of the left ventricle and implanting assistive devices such as pacemakers or defibrillators, do not restore function to damaged tissue. Moreover, while implantation of mechanical ventricular assist devices can provide long-term improvement in heart function, complications such as infection and blood clots remain problematic (Lietz, *Circulation*, 2007, 116:497-505). Although heart transplantation offers a viable option to replace damaged myocardium in selected individuals, organ availability and transplant rejection complications limit the widespread practical use of this approach.

Disclosed are methods for performing cardiac regeneration or repair using the disclosed subpopulations of cardiomyocytes. The methods can include delivering an effective amount of a subpopulation of cardiomyocytes to damaged heart muscle tissue in a subject in need of treatment. In some forms, the damaged heart muscle issue is a post-infarction scar. In some forms, the subpopulation of cardiomyocytes is derived from iPSCs originated from the subject's cells. In some forms, the subpopulation of cardiomyocytes is a $CD36^-$ subpopulation, which has a higher tolerance for hypoxia compared to a corresponding $CD36^+$ subpopulation and can increase the cell survival rate during cardiac regeneration or repair. In some forms, the subpopulation of cardiomyocytes is a $CD36^+$ subpopulation, which have more mature electrophysiological properties compared to a corresponding $CD36^-$ subpopulation and thus are less arrhythmogenic. Potentially lethal arrhythmias is a major limitation of CM transplantation. In some forms, the cardiomyocytes used for cardiac regeneration or repair contain a mixture of $CD36^+$ and $CD36^-$ subpopulations as a ratio that can overcome issues of cell survival rate and arrhythmia.

Thus, having identified and produced subpopulations of cardiomyocytes, the subpopulations can be mixed in defined ratios as desired to achieve different purposes, such as to increase the survival of transplanted cell or decrease the risk of arrhythmia. For example, cells of a $CD36^+$ subpopulation of cardiomyocytes and cells of a $CD36^-$ subpopulation of cardiomyocytes can be used in a ratio of 1:50, 1:45, 1:40, 1:35, 1:30, 1:25, 1:20, 1:15, 1:10, 1:8, 1:6, 1:5, 1:4, 1:3, 1:2, 1:1.5, 1:1.4, 1:1.3, 1:1.2, 1:1.1, 1:1, 1.1:1, 1.2:1, 1.3:1, 1.4:1, 1.5:1, 2:1, 3:1, 4:1, 5:1, 6:1, 8:1, 10:1, 15:1, 20:1, 25:1, 30:1, 35:1, 40:1, 45:1, or 50:1.

Methods of delivering the subpopulation of cardiomyocytes can include intravenous injection, direct infusion into the coronary arteries, direct injection into damaged tissue, or the use of cardiac tissue patches. These methods can be used in subjects whose blood flow has been restored to their hearts after a heart attack, provided that they do not have additional cardiac dysfunction that results in total occlusion or poor arterial flow. Of these two methods, intracoronary infusion offers the advantage of directed local delivery, thereby increasing the number of cells that reach the target tissue relative to the number that will home to the heart once they have been placed in the circulation. The subpopulation of cardiomyocytes can be also delivered through direct injection into the ventricular wall or damaged tissue of the subject. This endomyocardial injection approach can be carried out either via a catheter or during open-heart surgery (Oettgen, *Circulation*, 2006, 114:353-358). To determine the ideal site to inject the cells, additional steps can be performed to use mapping or direct visualization to identify the locations of scars and viable cardiac tissue.

The mechanism by which the subpopulation of cardiomyocytes promotes cardiac can involve one or more pathways. The transplanted cells may home to the damaged heart tissue and further forms new tissues, thereby strengthening the damaged heart tissue. Additionally, the transplanted cells may release growth factors and/or other molecules that promote blood vessel formation (angiogenesis) or stimulate resident cardiac stem cells to repair damage (Kocher, *Nat Med*, 2001, 7:430-436; Schuster, *Am J Physiol Heart Circ Physiol*, 2004, 287:H525-H532; Gnecchi, *Nat Med*, 2005, 11:367-368).

3. Actions Based on Identifications

The disclosed methods for applications of the subpopulations of cardiomyocytes include the determination, identification, indication, correlation, diagnosis, prognosis, etc. (which can be referred to collectively as "identifications") of subjects, diseases, conditions, states, etc., based on measurements, detections, comparisons, analyses, assays, screenings, etc. For example, cardiac drug screening involves determination of the responses of the subpopulations of cardiomyocytes to a specific compound. Such identifications are useful for many reasons. For example, and in particular, such identifications allow specific actions to be taken based on, and relevant to, the particular identification made. For example, diagnosis of a particular disease or condition in particular subjects (and the lack of diagnosis of that disease or condition in other subjects) has the very useful effect of identifying subjects that would benefit from treatment, actions, behaviors, etc., based on the diagnosis. For example, treatment for a particular disease or condition in subjects identified is significantly different from treatment of all subjects without making such an identification (or without regard to the identification). Subjects needing or that could benefit from the treatment will receive it and subjects that do not need or would not benefit from the treatment will not receive it.

Accordingly, also disclosed herein are methods comprising taking particular actions following and based on the disclosed identifications. For example, disclosed are methods comprising creating a record of an identification (in physical—such as paper, electronic, or other—form, for example). Thus, for example, creating a record of an identification based on the disclosed methods differs physically and tangibly from merely performing a measurement, detection, comparison, analysis, assay, screen, etc. Such a record is particularly substantial and significant in that it allows the identification to be fixed in a tangible form that can be, for example, communicated to others (such as those who could treat, monitor, follow-up, advise, etc., the subject based on the identification); retained for later use or review; used as data to assess sets of subjects, treatment efficacy, accuracy of identifications based on different measurements, detections, comparisons, analyses, assays, screenings, etc., and the like. For example, such uses of records of identifications can be made, for example, by the same individual or entity as, by a different individual or entity than, or a combination of the same individual or entity as and a different individual or entity than, the individual or entity that made the record of the identification. The disclosed methods of creating a record can be combined with any one or more other methods disclosed herein, and in particular, with any one or more steps of the disclosed methods of identification.

As another example, disclosed are methods comprising making one or more further identifications based on one or more other identifications. For example, particular treatments, monitorings, follow-ups, advice, etc. can be identified based on the other identification. For example, identification of a subject as having a disease or condition with a high level of a particular component or characteristic can be further identified as a subject that could or should be treated with a therapy based on or directed to the high level component or characteristic. A record of such further identifications can be created (as described above, for example) and can be used in any suitable way. Such further identifications can be based, for example, directly on the other identifications, a record of such other identifications, or a combination. Such further identifications can be made, for example, by the same individual or entity as, by a different individual or entity than, or a combination of the same individual or entity as and a different individual or entity than, the individual or entity that made the other identifications. The disclosed methods of making a further identification can be combined with any one or more other methods disclosed herein, and in particular, with any one or more steps of the disclosed methods of identification.

As another example, disclosed are methods comprising treating, monitoring, following-up with, advising, etc. a subject identified in any of the disclosed methods. Also disclosed are methods comprising treating, monitoring, following-up with, advising, etc. a subject for which a record of an identification from any of the disclosed methods has been made. For example, particular treatments, monitorings, follow-ups, advice, etc. can be used based on an identification and/or based on a record of an identification. For example, a subject identified as having a disease or condition with a high level of a particular component or characteristic (and/or a subject for which a record has been made of such an identification) can be treated with a therapy based on or directed to the high level component or characteristic. Such treatments, monitorings, follow-ups, advice, etc. can be based, for example, directly on identifications, a record of such identifications, or a combination. Such treatments, monitorings, follow-ups, advice, etc. can be performed, for example, by the same individual or entity as, by a different individual or entity than, or a combination of the same individual or entity as and a different individual or entity than, the individual or entity that made the identifications and/or record of the identifications. The disclosed methods of treating, monitoring, following-up with, advising, etc. can be combined with any one or more other methods disclosed herein, and in particular, with any one or more steps of the disclosed methods of identification.

The disclosed measurements, detections, comparisons, analyses, assays, screenings, etc., can be used in other ways and for other purposes than those disclosed. For example, study and/or research of cardiac development. Thus, the disclosed measurements, detections, comparisons, analyses, assays, screenings, etc. do not encompass all uses of such measurements, detections, comparisons, analyses, assays, screenings, etc.

The disclosed compositions and methods can be further understood through the following numbered paragraphs.

1. A subpopulation of mammalian stem cell- or mammalian progenitor cell-derived cardiomyocytes, wherein the subpopulation of cardiomyocytes comprises a portion of a population of mammalian stem cell- or mammalian progenitor cell-derived cardiomyocytes, wherein the subpopulation of cardiomyocytes is a $CD36^+$ subpopulation or a $CD36^-$ subpopulation, wherein the $CD36^+$ subpopulations has a higher proportion of cells expressing CD36 on the cell surface than the population of cardiomyocytes had, a higher average expression level of CD36 on the cell surface than the population of cardiomyocytes had, or a combination of both, wherein the $CD36^-$ subpopulation has a lower proportion of cells expressing CD36 on the cell surface than the population of cardiomyocytes had, a lower average expression level of CD36 on the cell surface than the population of cardiomyocytes had, or a combination of both.

2. The subpopulation of paragraph 1, wherein the subpopulation of cardiomyocytes was derived from the population of cardiomyocytes by selecting cells of the population that either (1) express CD36 on the cell surface or (2) do not express CD36 on the cell surface.

3. The subpopulation of paragraph 1, wherein the subpopulation of cardiomyocytes was derived from the population of cardiomyocytes by selecting cells of the population that either (1) express a relatively higher level of CD36 on the cell surface or (2) express a relatively lower level of CD36 on the cell surface.

4. The subpopulation of any one of paragraphs 1-3, wherein the population of cardiomyocytes was derived from human stem cells or human progenitor cells.

5. The subpopulation of any one of paragraphs 1-4, wherein the population of cardiomyocytes was derived from totipotent stem cells or pluripotent stem cells.

6. The subpopulation of paragraph 5, wherein the population of cardiomyocytes was derived from embryotic stem cells or induced pluripotent stem cells.

7. The subpopulation of paragraph 6, wherein the population of cardiomyocytes was derived from human embryotic stem cells Line H7 or H9.

8. The subpopulation of paragraph 6, wherein the population of cardiomyocytes was derived from MD1 human induced pluripotent stem cells.

9. The subpopulation of any one of paragraphs 1-8, wherein the subpopulation of cardiomyocytes is the $CD36^+$ subpopulation.

10. The subpopulation of paragraph 9, wherein the proportion of cells of the subpopulation of cardiomyocytes expressing CD36 on the cell surface is different than the proportion of cells of the population of cardiomyocytes expressing CD36 on the cell surface by a factor of between about 1.5 and about 10.

11. The subpopulation of paragraph 9 or paragraph 10, wherein the subpopulation of cardiomyocytes has a lower spontaneous beating frequency, a higher proportion of binucleated cells, higher expression of one or more sarcomeric proteins involved in cardiac maturation, higher expression of one or more ion channels involved in cardiac maturation, lower expression of one or more extracellular matrix proteins, lower expression of one or more cell adhesion proteins, higher expression of one or more genes involved in mitochondrial function, higher expression of one or more centromeric genes, higher expression of one or more genes associated with DNA repair, higher mitochondrial content, more polarized mitochondrial membrane potential, higher ATP production, higher cellular uptake of long-chain fatty acids, larger increase in mitochondrial membrane potential when fed with long-chain fatty acids, or combinations thereof, as compared to the CD36⁻ subpopulation from the same population of cardiomyocytes.

12. The subpopulation of any one of paragraphs 1-8, wherein the subpopulation of cardiomyocytes is the CD36⁻ subpopulation.

13. The subpopulation of paragraph 12, wherein the proportion of cells of the subpopulation of cardiomyocytes not expressing CD36 on the cell surface is different than the proportion of cells of the population of cardiomyocytes not expressing CD36 on the cell surface by a factor of between about 1.5 and about 10.

14. The subpopulation of paragraph 12 or paragraph 13, wherein the subpopulation of cardiomyocytes has a higher spontaneous beating frequency, a lower proportion of binucleated cells, lower expression of one or more sarcomeric proteins involved in cardiac maturation, lower expression of one or more ion channels involved in cardiac maturation, higher expression of one or more extracellular matrix proteins, higher expression of one or more cell adhesion proteins, lower expression of one or more genes involved in mitochondrial function, lower expression of one or more centromeric genes, lower expression of one or more genes associated with DNA repair, lower mitochondrial content, less polarized mitochondrial membrane potential, lower ATP production, lower cellular uptake of long-chain fatty acids, smaller increase in mitochondrial membrane potential when fed with long-chain fatty acids, or combinations thereof, as compared to the CD36⁺ subpopulation from the same population of cardiomyocytes.

15. The subpopulation of paragraph 11 or paragraph 14, further defined by one or more of the following features:
the one or more sarcomeric proteins involved in cardiac maturation comprise TNNI3, MYL2, or a combination thereof;
the one or more ion channels involved in cardiac maturation comprise KCNJ2;
the one or more extracellular matrix proteins comprise COL8A1;
the one or more cell adhesion proteins comprise NRP2;
the one or more genes involved in mitochondrial function comprise ATP5G4, ACADM, or a combination thereof;
the one or more centromeric genes comprises CENPH, CENPM, or a combination thereof; and
the one or more genes associated with DNA repair comprises EXO1, CDK1, or a combination thereof.

16. The subpopulation of any one of paragraphs 1-15, wherein the cells of the subpopulation of cardiomyocytes express one or more markers associated with a cardiac phenotype, wherein the one or more markers are selected from CD172A, TNNT2, and a combination thereof.

17. A method to isolate the subpopulation of cardiomyocytes of any one of paragraphs 1-16, comprising:

(a) culturing mammalian stem cell- or mammalian progenitor cell-derived cardiomyocytes for a time period sufficient for expression of CD36 on the cell surface of some of the cardiomyocytes;
(b) either:
(b1) isolating those of the cardiomyocytes (1) expressing CD36 on the cell surface or (2) not expressing CD36 on the cell surface to yield the subpopulation of cardiomyocytes, or
(b2) isolating those of the cardiomyocytes (1) expressing a relatively higher level of CD36 on the cell surface or (2) expressing a relatively lower level of CD36 on the cell surface to yield the subpopulation of cardiomyocytes.

18. The method of paragraph 17, wherein the time period in step (a) is between about 2 and about 150 days, between about 10 and about 120 days, between about 15 and about 90 days, or between about 30 and about 60 days.

19. The method of paragraph 17 or paragraph 18, wherein step (b1) comprises:
(i) contacting the cardiomyocytes from step (a) with a sorting agent that is specific for CD36 under conditions sufficient to allow binding of the sorting agent to CD36 on the cell surface of the cardiomyocytes; and
(ii) isolating those of the cardiomyocytes to which the sorting agent (1) has bound or (2) has not bound to yield the subpopulation of cardiomyocytes.

20. The method of paragraph 17 or paragraph 18, wherein step (b2) comprises:
(i) contacting the cardiomyocytes from step (a) with a sorting agent that is specific for CD36 under conditions sufficient to allow binding of the sorting agent to CD36 on the cell surface of the cardiomyocytes; and
(ii) isolating those of the cardiomyocytes to which the sorting agent (1) has bound at a relatively higher level or (2) has bound at a relatively lower level to yield the subpopulations of cardiomyocytes.

21. The method of paragraph 19 or paragraph 20, wherein the sorting agent comprises an antibody specific for CD36.

22. The method of any one of paragraphs 17-21, wherein in step (b) the subpopulation of cardiomyocytes is isolated using fluorescence-activated cell sorting or magnetic-activated cell sorting.

23. The method of any one of paragraphs 17-22, further comprising an additional step prior to step (b), wherein the additional step comprises sorting or separating cardiomyocytes from non-cardiomyocyte cells by isolating cells expressing CD127A on the cell surface.

24. A method to model a cardiac disease or disorder using the subpopulation of cardiomyocytes of any one of paragraphs 1-16, comprising:
(a) inducing the cardiac disease or disorder in the subpopulation of cardiomyocytes; and
(b) characterizing the cardiac disease or disorder in the subpopulation of cardiomyocytes from step (a).

25. A method to screen drugs or therapies for a cardiac disease or disorder using the subpopulation of cardiomyocytes of any one of paragraphs 1-16, comprising:
(a) inducing the cardiac disease or disorder in the subpopulations of cardiomyocytes;
(b) treating the subpopulations of cardiomyocytes from step (a) with an effective amount of one or more candidate compounds or therapies; and
(c) evaluating the efficacy of the candidate compound or therapy in reducing one or more symptoms of the cardiac disease or disorder.

26. The method of paragraph 24 or paragraph 25, wherein the cardiac disease or disorder is cardiac arrhythmia.

27. The method of any one of paragraphs 24-26, wherein the cardiac disease or disorder is induced by doxorubicin-induced cardiotoxicity, long QT syndrome, Brugada syndrome, genetic heart disease, amyloidosis, progeria, diabetic coma, jellyfish intoxication, hyperthyroidism, Yellow Fever, Chagas disease, aortic valve regurgitation, prescription drug abuse leading to arrhythmia, Rett syndrome, myocarditis, tricuspid atresia, Lyme disease, Churg-Strauss syndrome, forms of heart disease or failure involving arrhythmia, enlarged heart, broken heart syndrome, thyroid nodules, atrioventricular canal defect, cholera, mitral valve stenosis, multiple system atrophy (MSA), snoring, mitral valve prolapse, amniotic fluid embolism, gangrene, aplastic anemia, congenital heart disease in adults, heat exhaustion, Graves' disease, cardiomyopathy, premature ventricular contractions, Bradycardia, fatigue, tachycardia, dizziness or shortness of breath, diabetes, arrhythmogenic right ventricular cardiomyopathy, dilated or hypertrophic cardiomyopathies, or muscular dystrophies optionally selected from Duchenne and Becker muscular dystrophies and mitochondrial diseases.

28. The method of any one of paragraphs 24-27, wherein the subpopulation of cardiomyocytes is derived from induced pluripotent stem cells of a patient with the cardiac disease or disorder.

29. The method of paragraph 28, wherein step (a) is void.

30. A method to assess the cardiotoxic effect of a compound using the subpopulation of cardiomyocytes of any one of paragraphs 1-16, comprising:
(a) contacting the compound with the subpopulation of cardiomyocytes; and
(b) measuring the cardiotoxic effect of the compound on the subpopulation of cardiomyocytes.

31. A method to assess the metabolic maturation of cardiomyocytes, comprising measuring the expression level of CD36 on the cell surface of the cardiomyocytes, wherein a higher expression level of CD36 corresponds to a more metabolic mutation state of the cardiomyocytes.

32. The method of paragraph 31, wherein the cardiomyocytes are derived from mammalian stem cells or mammalian progenitor cells.

33. The method of paragraph 32, wherein the cardiomyocytes are derived from human stem cells or human progenitor cells.

34. A system that models a cardiac disease or disorder comprising the subpopulation of cardiomyocytes of any one of paragraphs 1-16.

35. The system of paragraph 34, wherein the cardiac disease or disorder is cardiac arrhythmia.

36. The system of paragraph 34 or paragraph 35, wherein the cardiac disease or disorder is induced by doxorubicin-induced cardiotoxicity, long QT syndrome, Brugada syndrome, genetic heart disease, amyloidosis, progeria, diabetic coma, jellyfish intoxication, hyperthyroidism, Yellow Fever, Chagas disease, aortic valve regurgitation, prescription drug abuse leading to arrhythmia, Rett syndrome, myocarditis, tricuspid atresia, Lyme disease, Churg-Strauss syndrome, forms of heart disease or failure involving arrhythmia, enlarged heart, broken heart syndrome, thyroid nodules, atrioventricular canal defect, cholera, mitral valve stenosis, multiple system atrophy (MSA), snoring, mitral valve prolapse, amniotic fluid embolism, gangrene, aplastic anemia, congenital heart disease in adults, heat exhaustion, Graves' disease, cardiomyopathy, premature ventricular contractions, Bradycardia, fatigue, tachycardia, dizziness or shortness of breath, diabetes, arrhythmogenic right ventricular cardiomyopathy, dilated or hypertrophic cardiomyopathies, or muscular dystrophies optionally selected from Duchenne and Becker muscular dystrophies and mitochondrial diseases.

VII. EXAMPLES

Example 1. Identifying CD36 as a Maturation Marker for Pluripotent Stem Cell-Derived Cardiomyocytes Identification of Cell Surface Markers for Cardiac Maturation Cell surface capture (CSC) technology is a chemoproteomic-based method to selectively label, capture, and identify extracellular-exposed cell surface N-glycoproteins from cells (Bausch-Fluck, et al., *Methods Mol Biol.*, 2012, 909: 1-16; Boheler and Gundry (Editors), The Surfaceome: Methods and Protocols, Methods in Molecular Biology, 2018).

The surface proteome of Days (Ds) 15, 30, 60, and 90 Line 7 human embryonic stem cell (hESC)-derived CMs (hESC-CMs) was profiled to identify potential markers of cardiac maturation, using the CSC technology. CSC labeling were performed on CM populations that were >95% positive for cardiac Troponin T (TNNT2). Altogether, 582 N-glycoproteins were identified on the cell surface of hESC-CMs. The tags included predicted transmembrane (79.7%), glycosylphosphatidylinositol (GPI)-linked (5.7%), and extracellular matrix (4.8%) proteins.

Figure 1D:
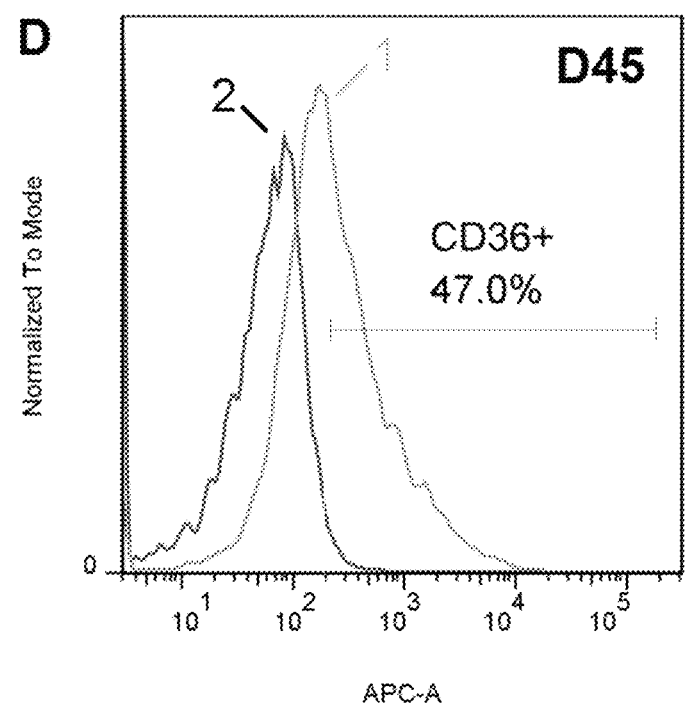
Figure 1E:
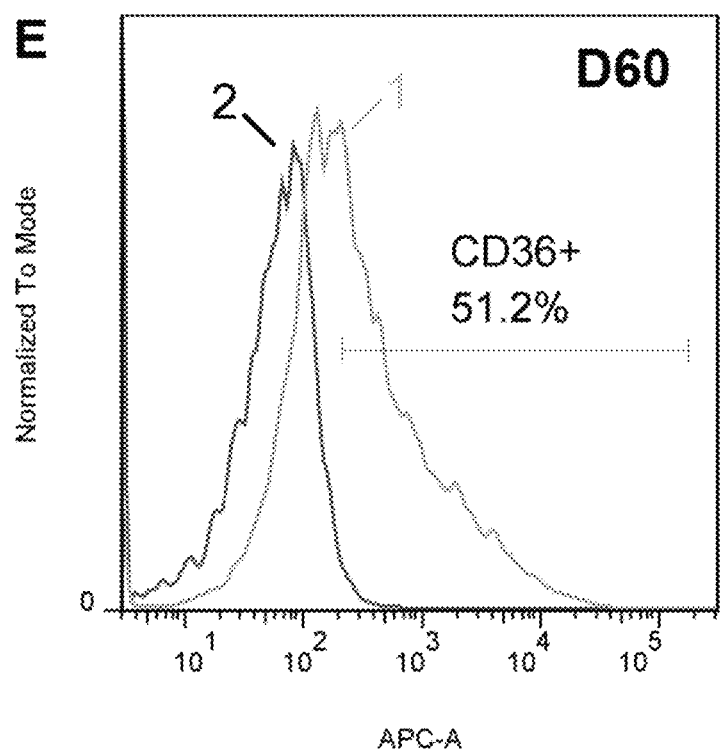

Comparisons were performed with the cell surface protein atlas to exclude ubiquitously expressed proteins. Special attention was paid to cluster of differentiation (CD) proteins (for which antibodies exist) that were abundant at late stages of differentiation (D60 and D90), but were absent or present at low levels at early stages (D15 and D30). The only protein that fulfilled these criteria was CD36, a fatty acid translocase implicated in fatty acid beta-oxidation, a process associated with more adult-like heart function (Kim and Dyck, *Biochim Biophys Acta*, 2016, 1860(10):1450-60). Iterative RNA and protein analyses revealed that CD36 was up-regulated in CMs during mouse and human development and during in vitro differentiation of hESC. Flow cytometric experiments showed that CD36 was largely absent from hESC-CMs on D15, and that its presence increased with time of cultivation, but only in a sub-population of CMs (FIGS. 1A-1E). On D45 to D60, ~50% of the CMs presented this marker on the cell surface (FIGS. 1D and 1E). Taken together, these data showed that CD36 expression was positively associated with maturation stage of CMs.

To determine if CD36 marked a subpopulation with a more advanced developmental state, CD36$^+$ and CD36$^-$ subpopulations were isolated by fluorescence-activated cell sorting from D45 hESC-CMs. Since CD36 itself is not specific to CMs, an established cardiac marker, CD172A (Dubois, et al., *Nat Biotechnol*, 2011, 29:1011-1018), was included to ensure that the sorted cells consisted of CMs only. Re-plated CD172A$^+$/CD36$^+$ and CD172A$^+$/CD36$^-$ CMs were morphologically similar and were positive for α-actinin. When examined more closely, the CD172A$^+$/CD36$^+$ and CD172A$^+$/CD36$^-$ CMs had distinct phenotypic differences. CD172A$^+$/CD36$^+$ CMs had a significantly lower spontaneous beating frequency (12.1±1.5 vs. 24.6±3.0 beats per min, p<0.001), a higher proportion of binucleated cells (9.9±0.8 vs. 4.5±0.8, p<0.03). These cellular traits of CD172A$^+$/CD36$^+$ CMs are all consistent with a more mature phenotype.

RNA Sequencing Analysis of Subpopulations of CMs

Genome-wide gene expression profiling was performed by RNA sequencing to define the molecular signatures of CD172A$^+$/CD36$^{+/-}$, CD172A$^+$/CD36$^+$, and CD172A$^+$/CD36$^-$ hESC-CMs. Differentially expressed genes between CD172A$^+$/CD36$^+$ and CD172A$^+$/CD36$^-$ CMs were analyzed using DSeq2, and 299 up- and 633 down-regulated genes with fold differences >1.4 and p<0.05 were identified. As expected, CD36 mRNA and protein levels were significantly elevated in CD172A$^+$/CD36$^+$ CMs by 12.9±3.2 and 4.0±1.1 fold respectively, relative to CD172A$^+$/CD36$^-$ CMs. The transcriptomes of the different cell populations were similar, but some notable RNA differences were observed. Examples included a limited number of sarcomeric proteins (e.g., TNNI3 and MYL2) and ion channels (e.g., KCNJ2) implicated in cardiac maturation. Conversely, genes commonly associated with cardiac identify such as TNNT2 and SIRPA (CD172A) were similar in all subpopulations, confirming that all subpopulations were CMs. Functional annotation revealed that the genes most significantly down-regulated in CD172A$^+$/CD36$^+$ CMs involved transcripts encoding proteins of the extracellular matrix (e.g., COL8A1) and cell adhesion (e.g., NRP2). By contrast, the up-regulated genes were significantly involved in mitochondrial function (Table 1), including transcripts for oxidative phosphorylation (ATP5G4) and fatty acid oxidation (ACADM); however, genes involved in glycolysis (e.g., PGM1, ENO2, etc.) did not differ between CD172A$^+$/CD36$^+$ and CD172A$^+$/CD36$^-$ CMs. Other upregulated genes in CD172A$^+$/CD36$^+$ CMs include centromeric genes such as CENPH and CENPM, which may underlie the binucleation phenotype of these cells. Interesting, levels of genes associated with DNA repair, such as EXO1 and CDK1, were higher in CD172A$^+$/CD36$^+$ CMs. These genes act as checkpoints to initiate apoptosis upon the detection of DNA damage, and higher levels of these genes may indicate susceptibility to apoptosis. qRT-PCR and Western blot analyses of selected genes validated the RNA sequencing results. Altogether, the significant elevation of metabolic and mitochondrial proteins in the CD172A$^+$/CD36$^+$ CMs suggested a more advanced metabolic state defined by the presence of CD36.

TABLE 1

Top gene ontology groups upregulated in CD172A$^+$CD36$^+$ CMs compared with CD172A$^+$CD36$^-$ CMs.

| Term | P value |
| --- | --- |
| GO:0006123~mitochondrial electron transport, cytochrome c to oxygen | 8.11E−11 |
| GO:1902600~hydrogen ion transmembrane transport | 1.20E−06 |
| GO:0007062~sister chromatid cohesion | 8.04E−06 |
| GO:0042776~mitochondrial ATP synthesis coupled proton transport | 1.42E−04 |
| GO:0019915~lipid storage | 2.44E−04 |
| GO:0007059~chromosome segregation | 2.56E−04 |
| GO:0000070~mitotic sister chromatid segregation | 2.87E−04 |
| GO:0006120~mitochondrial electron transport, NADH to ubiquinone | 4.31E−04 |
| GO:0006281~DNA repair | 0.001058 |

Functional Analysis of Subpopulations of CMs

Figure 2A:
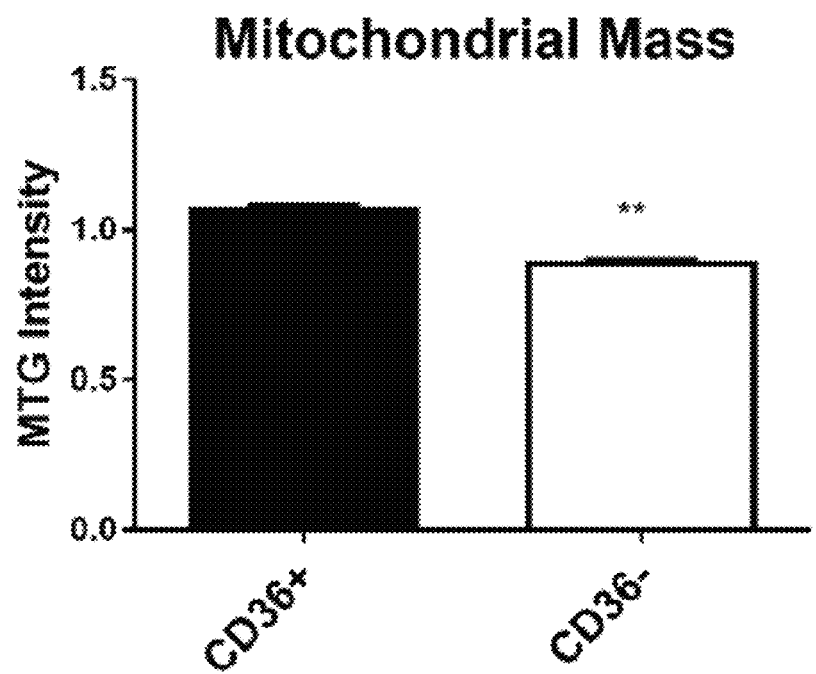
FIGS. 2A-2E are bar graphs showing the relative levels of mitochondrial mass (A), mitochondrial DNA ND1 (B) and ND5 (C), mitochondrial membrane potential $\Delta\psi_m$ (D), and ATP production (E) in CD172A$^+$/CD36$^+$ (black) and CD172A$^+$/CD36$^-$ (white) hESC-CMs. The relative levels of mitochondrial mass, mitochondrial membrane potential, and ATP production were determined using MitoTracker™ green (MTG) staining (n=4), tetramethylrhodamine ethyl ester (TMRE) staining (n=7, calibrated by mitochondrial mass based on the result of MTG staining), and CellTiter-Glo® luminescent assay (n=5), respectively. High TMRE intensity indicates polarized mitochondrial membrane potential. *p<0.05, p<0.01, *p<0.001.
Figure 2B:
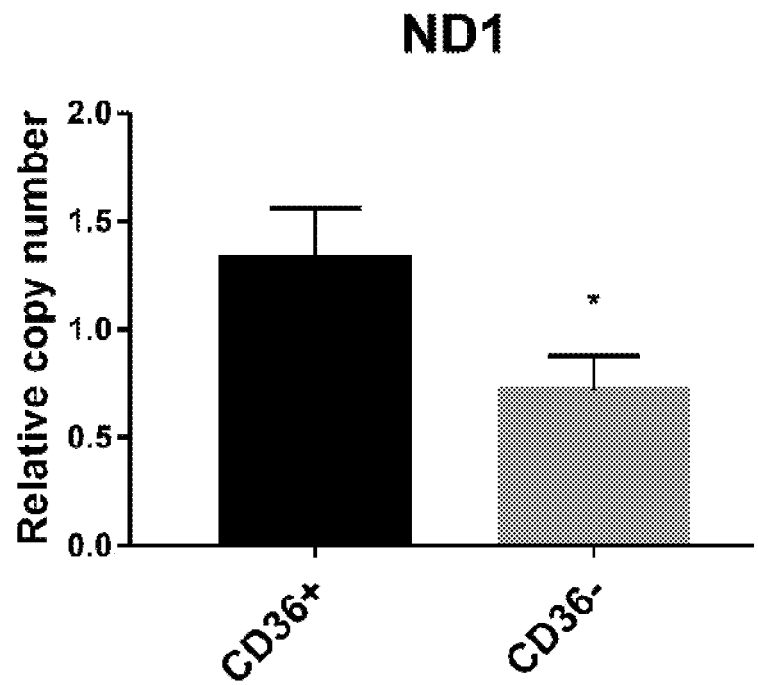
Figure 2C:
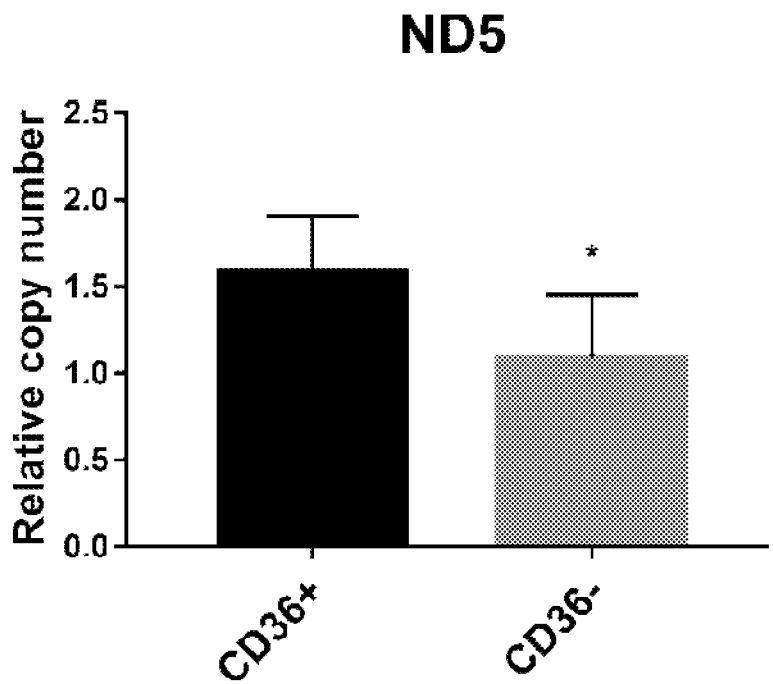
Figure 2D:
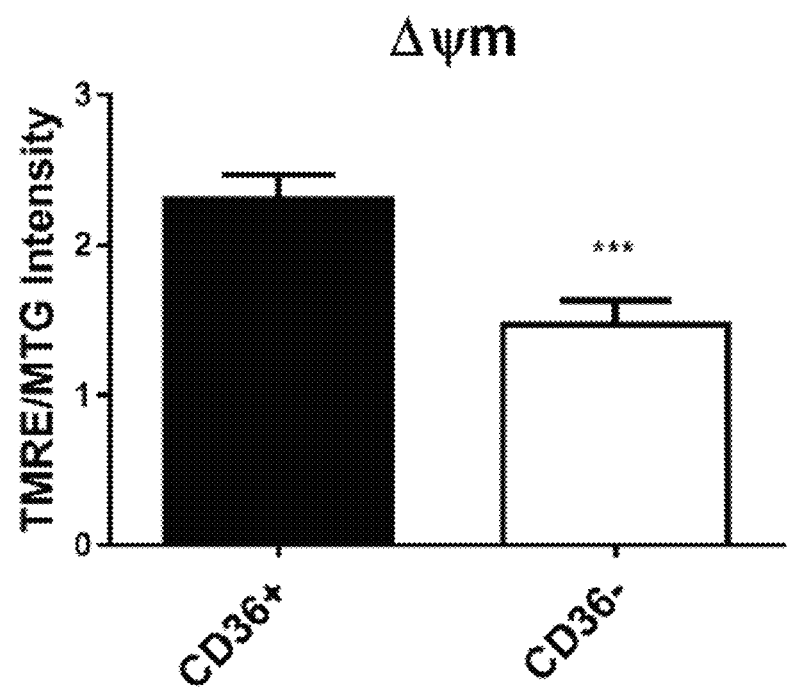
Figure 2E:
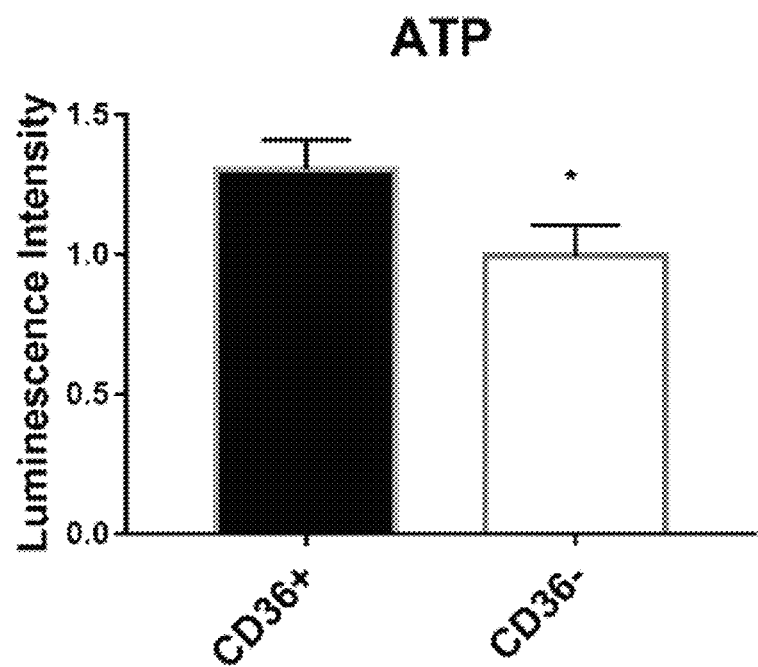

Functional analyses of the CM subpopulations was conducted to examine their mitochondrial and metabolic properties in hESC-CMs. CD172A$^+$/CD36$^+$ CMs had a significantly higher mitochondrial content compared to CD172A$^+$/CD36$^-$ CMs, as revealed by mitochondrial DNA mass (FIG. 2A) and mitochondrial DNA copy numbers (FIGS. 2B and 2C). The mitochondrial output of the CM subpopulations was assessed using two parameters: mitochondrial membrane potential ($\Delta\psi_m$) and ATP production. $\Delta\psi_m$ was measured using a potentiometric dye, tetramethylrhodamine ethyl ester (TMRE). Compared to CD172A$^+$/CD36$^-$ CMs, CD172A$^+$/CD36$^+$ CMs had a significantly more polarized $\Delta\psi_m$ (FIG. 2D), and their mitochondria adopted a more elongated and parallel arrangement, suggestive of a more adult-like phenotype. ATP production was measured using the CellTiter-Go® assay and was similarly increased in CD172A$^+$/CD36$^+$ CMs (FIG. 2E).

Figure 3A:
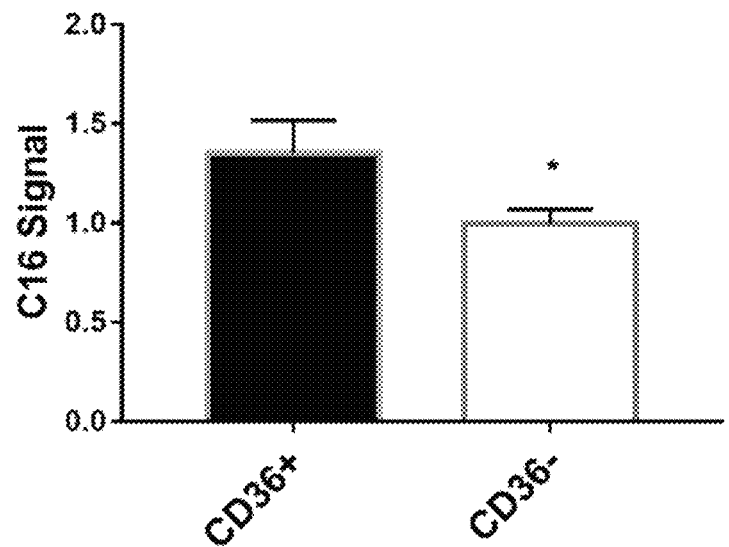
FIG. 3A is a bar graph showing the uptake of fatty acid (FA) by CD172A$^+$/CD36$^+$ (black) and CD172A$^+$/CD36$^-$ (white) hESC-CMs. The FA uptake assay was performed using a BODIPY-labeled C16 palmitate analog (n=6).
Figure 3B:
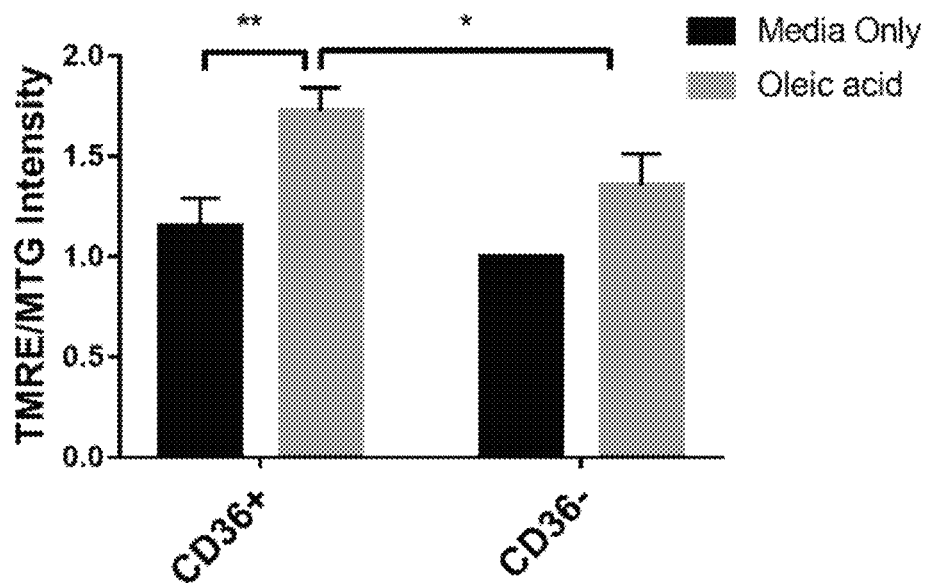
FIG. 3B is a bar graph showing the relative levels of mitochondrial membrane potential $\Delta\psi_m$ in CD172A$^+$/CD36$^+$ and CD172A$^+$/CD36$^-$ hESC-CMs cultured in the absence (black) and presence (gray) of oleic acid (n=5). The $\Delta\psi_m$ values were measured using TMRE staining (calibrated by mitochondrial mass based on the result of MTG staining) and normalized to the $\Delta\psi_m$ value of CD172A$^+$/CD36$^-$ hESC-CMs in the absence of oleic acid. *p<0.05, p<0.01, *p<0.001.

In addition to enhanced mitochondrial output, adult CMs were characterized by their preference for fatty acid as fuel for energy production. In CMs, CD36 functions as a fatty acid translocase to facilitate the uptake of long-chain fatty acids such as palmitic and oleic acids, thus increased level of this protein is expected to enhance fatty acid entry into cells. Consistent with this notion, the cellular uptake of a fluorescently-labeled C16-palmitate analog was significantly enhanced by 35.9% in CD172A$^+$/CD36$^+$ CMs compared to CD172A$^+$/CD36$^-$ CMs (FIG. 3A). Additional experiments were performed to test whether increased fatty acid uptake led to increased metabolic output. When cultured in nutrient-deficient media lacking fatty acids, CD172A$^+$/CD36$^+$ and CD172A$^+$/CD36$^-$ CMs had similar $\Delta\psi_m$. Supplementation with oleic acid significantly increased the magnitude of $\Delta\psi_m$ in both subpopulation of CMs, but the increase was more pronounced in CD172A$^+$/CD36$^+$ CMs (43.0%) compared to CD172A$^+$/CD36$^-$ CMs (22.9%), indicating enhanced fatty acid utilization in the former (FIG. 3B). Taken together, the experimental results showed that CD172A$^+$/CD36$^+$ CMs display mitochondrial properties indicative of a more adult-like phenotype.

The presence of a sub-population of CD36$^+$ CMs is conserved across hPSC lines. In MD1 hiPSC and H9 hESC cell lines, CD36$^+$ cells can be identified as a subpopulation of CD172A$^+$ CMs, although the proportion of CD36$^+$ CMs varies [MD1: ~50% (30-81%), approximately D45; H9: ~36% (18-72%), approximately D45]. CD36$^+$ hiPSC-CMs (like their hESC counterparts) always had a more polarized $\Delta\psi_m$ than the corresponding CD36$^-$ CMs. To compare variations among hPSC samples and lines, the same CD36 threshold was applied to all samples such that the CD36$^+$ subpopulations defined here can have similar levels of this protein. The coefficient of variation of $\Delta\psi_m$ was significantly reduced in CD36$^+$ CMs compared to CD36$^{+/-}$ CMs. Isolation of CD36$^+$ CMs thus significantly decreased the interline heterogeneity among hPSC-CMs.

Figure 4A:
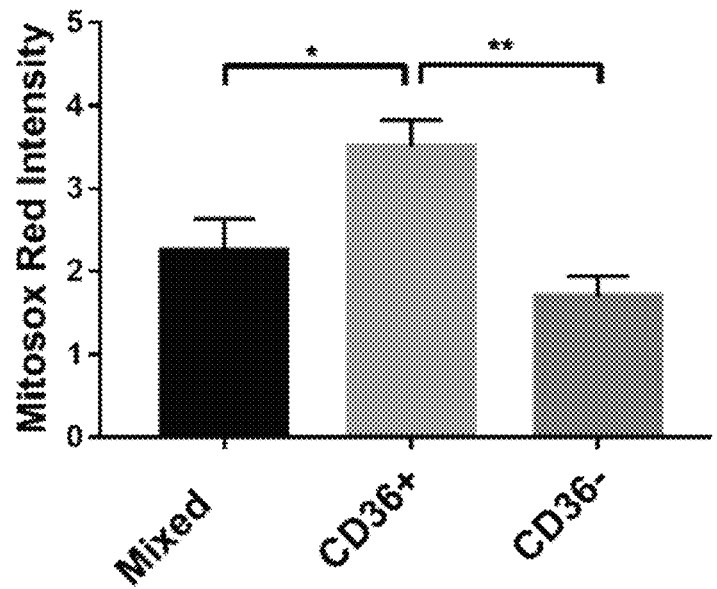
FIGS. 4A-4D are bar graphs showing the relative levels of mitochondrial superoxide (A), mitochondrial membrane potential $\Delta\psi_m$ (B), nuclear condensation (C), and cell viability (D) in CD172A$^+$/CD36$^{+/-}$, CD172A$^+$/CD36$^+$, and CD172A$^+$/CD36$^-$ hECS-CMs after exposure to 100 μM hydrogen peroxide for 30 min. The relative levels of mitochondrial superoxide, mitochondrial membrane potential, nuclear condensation, and cell viability were determined using the MitoSOX™ red dye (n=5), TMRE staining (n=5, calibrated by mitochondrial mass based on the result of MTG staining), Hoechst staining (n=5), and PrestoBlue® staining (n=9), respectively. *p<0.05, p<0.01, *p<0.001.
Figure 4B:
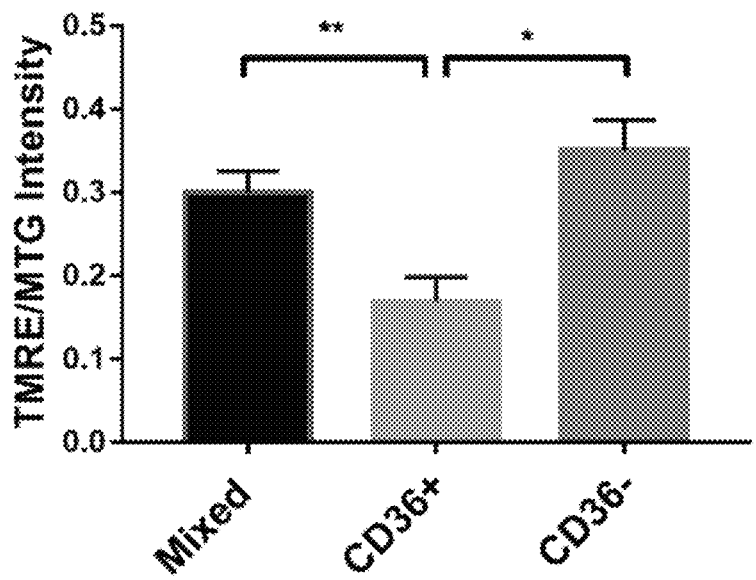
Figure 4C:
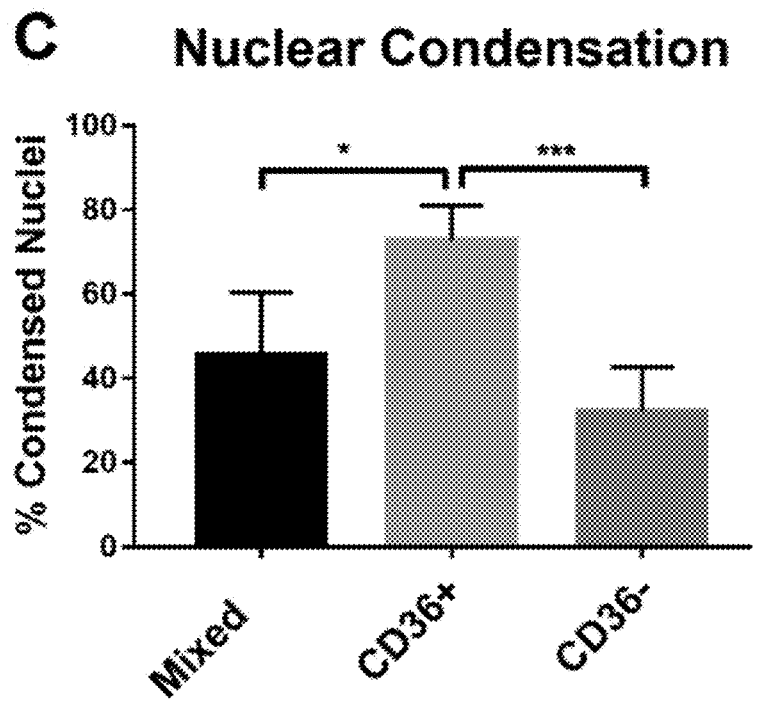
Figure 4D:
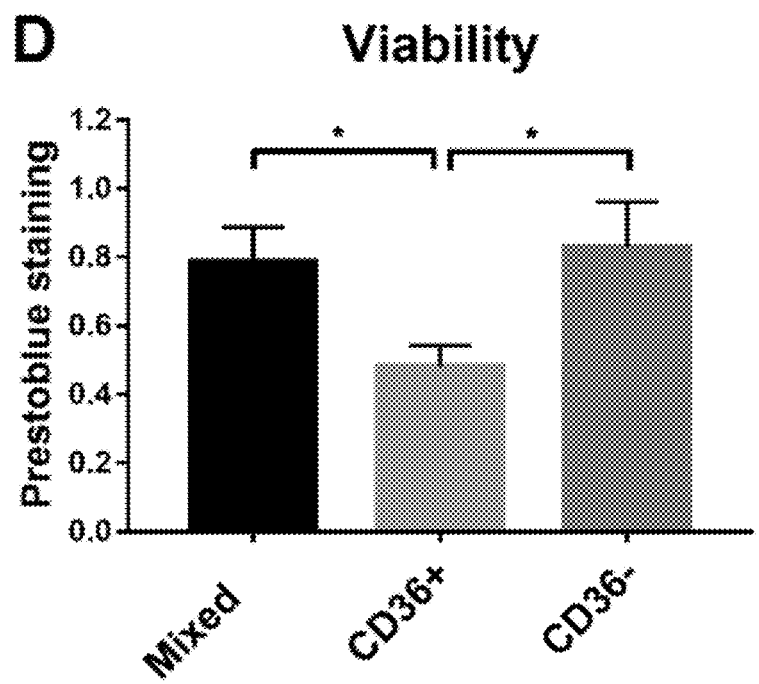

The responses of mitochondrial function to oxidative stress were examined in subpopulations of hESC-CMs. Addition of hydrogen peroxide promoted the production of a higher level of reactive oxygen species (ROS) in the form of mitochondrial superoxide in CD172A$^+$/CD36$^+$ CMs compared to CD172A$^+$/CD36$^{+/-}$ and CD172A$^+$/CD36$^-$ CMs as revealed by the MitoSOX™ red dye (CD172A$^+$/CD36$^{+/-}$: 2.2±0.4 fold vs. CD172A$^+$/CD36$^+$: 3.5±0.3 fold vs. CD172A$^+$/CD36$^-$: 1.7±1.2 fold) (FIG. 4A). The increase in the superoxide level resulted in a greater depolarization of $\Delta\psi_m$ (CD172A$^+$/CD36$^{+/-}$: 0.30±0.03 vs. CD172A$^+$/CD36$^+$:

0.17±0.03 vs. CD172A$^+$/CD36$^-$: 0.35±0.04) (FIG. 4B), concomitant with a dramatic increase in nuclear condensation (CD172A$^+$/CD36$^{+/-}$: 46±15% vs. CD172A$^+$/CD36$^+$: 73±8% vs. CD172A$^+$/CD36$^-$: 32%±11%) (FIG. 4C) and a decrease in overall cell viability (CD172A$^+$/CD36$^{+/-}$: 94.7±10% vs. CD172A$^+$/CD36$^+$: 57±6% vs. CD172A$^+$/CD36$^-$: 104%±13%) (FIG. 4D). Therefore, CD172A$^+$/CD36$^+$ CMs are more susceptible to ROS damage and cell death.

In summary, CD36 is a cell surface marker that can identify well-defined and mature CMs from in vitro differentiated CMs. Consistent with the established role of CD36 as a protein important for metabolism, CMs positive for CD36 readily uptake and utilize fatty acids as substrates, have a higher content of mitochondria, more polarized $\Delta\psi_m$, and higher ATP production, and are more sensitive to oxidative stress than cells lacking this surface marker. Isolation of the CMs with similar levels of CD36 decreases interline variability and permits a more consistent evaluation of mitochondrial function from diverse hPSC lines. CD172A$^+$CD36$^+$ CMs can be utilized as a surrogate model of oxidative stress-induced cardiomyocyte apoptosis during ischemia/reperfusion (I/R) injuries. The results confirmed mitochondrial damage as a key mediator of I/R-induced cell death. Use of earlier hPSC-CMs or unsorted cells lead to a less consistent outcome, due to the embryonic-like nature of the CMs which are more tolerant of oxidative stress and thus may not accurately recapitulate the damage response seen in adult patients. CD172A$^+$CD36$^+$ CMs showed increased sensitivity and more severe damage, thereby more closely mimicking the adult phenotype. The use of CD172$^+$CD36$^+$ CM subpopulations, with more mature mitochondria and increased sensitivities to oxidative stress, can greatly advance the study of human adult disease phenotypes that involve mitochondrial dysfunction.

Example 2. Modeling Cardiotoxicity Using Subpopulations of Cardiomyocytes

Doxorubicin-Induced Cardiotoxicity (DCT)

Doxorubicin (dox) is an effective chemotherapeutic agent for the treatment of a wide variety of malignancies, but is associated with irreversible and potentially lethal myocardial damage. Cancer survivors exposed to dox have a much-increased risk of cardiac complications compared to the general population. At doses exceeding 550 mg/m$^2$, the incidence of congestive heart failure exceeds 30%, with potentially lethal consequences.

Years of animal experimentation and numerous clinical trials yielded only one partially-effective treatment, dexrazoxane. However, dexrazoxane reduces the tumor response rate to dox. Of even more concern, a threefold increase in the incidence of second primary malignancies (myelodysplastic syndrome and acute myeloid leukemia) in dexrazoxane-treated pediatric patients was reported in two randomized studies. Consequently, dexrazoxane is only approved for the treatment of a small subset of patients. The vast majority of patients who receive dox treatment are unprotected from its cardiotoxic effects. Therefore, it is critical to improve the mechanistic understanding of doxorubicin-induced cardiotoxicity (DCT) and identify alternative treatment for this life-threatening disorder.

Using PSC-CMs to Model DCT

Human pluripotent stem cells (hPSCs) can be generated from embryos [human embryonic stem cells (hESC)] or induced from somatic cells [human induced pluripotent stem cells (hiPSC)]. hPSCs can self-renew and represents an unlimited cell source for CMs. Dox treatment of hPSC-CMs can produce many features of DCT; however, hPSC-CMs do not recapitulate patient responses to treatment. Dexrazoxane, the only FDA-approved treatment for DCT, failed to protect hPSC-CMs. Conversely, N-acetylcysteine, which is effective in mouse models of DCT but was unsuccessful in clinical trials, rescued hPSC-CMs. These inappropriate responses were attributed to the immaturity of hPSC-CMs and lower mitochondrial density. hPSC-CMs, as currently utilized, are inadequate models to evaluate treatment against DCT. hPSC-CMs with improved mitochondrial properties are needed to overcome this problem.

Figure 5A:
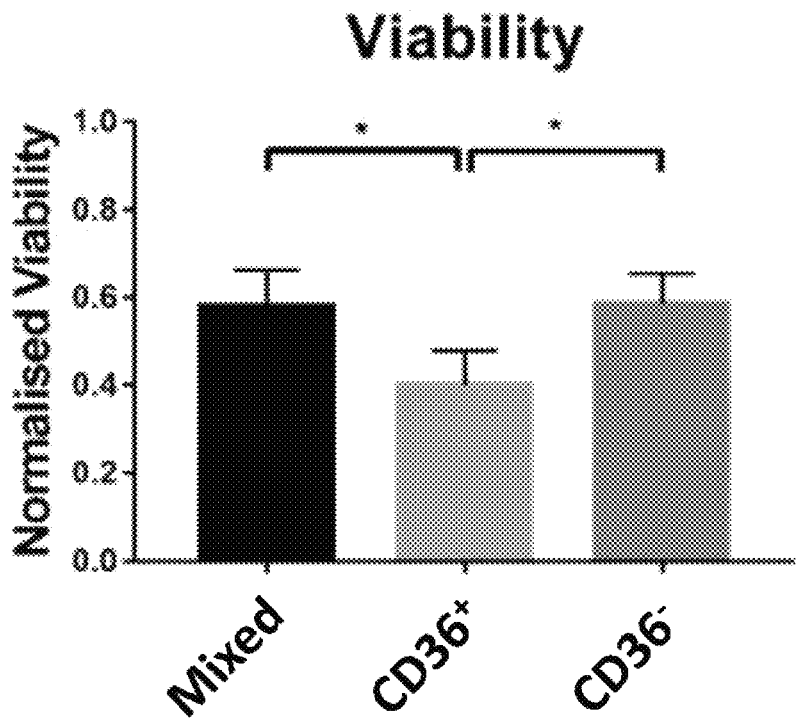
FIGS. 5A and 5B are bar graphs showing the normalized levels of cell viability (A) and mitochondrial membrane potential $\Delta\psi_m$ (B) of mixed (unsorted) hESC-CMs, CD36$^+$ hESC-CMs, and CD36$^-$ hESC-CMs after exposure to doxorubicin (dox). The hESC-CMs were treated with 1 mM dox for 24 hrs. Cell viability and mitochondrial membrane potential $\Delta\psi_m$ were determined by the XTT and TMRE/MTG assays (n=9 and 7), respectively, and normalized to untreated hESC-CMs.
Figure 5B:
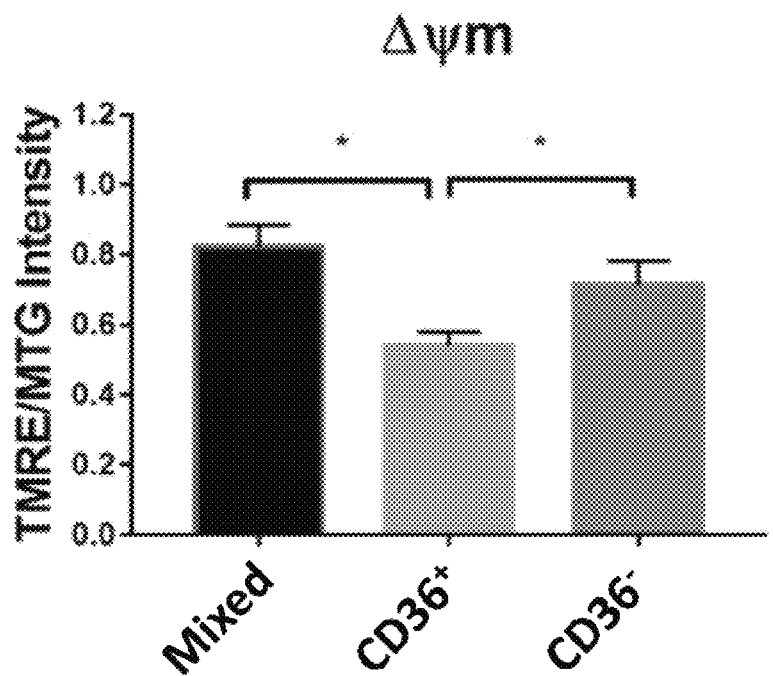
Figure 5C:
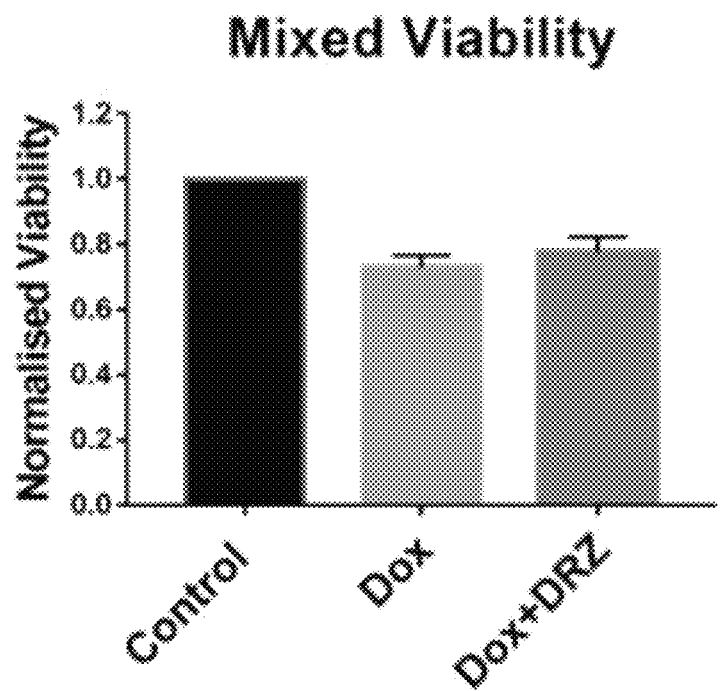
FIGS. 5C-5H are bar graphs showing the effect of dexrazoxane (DRZ), an active compound in reducing dox-induced cardiotoxicity, on the normalized levels of cell viability and mitochondrial membrane potential $\Delta\psi_m$ of mixed (unsorted) hESC-CMs, CD36$^+$ hESC-CMs, and CD36$^-$ hESC-CMs after exposure to dox. (C) and (D): viability and $\Delta\psi_m$ for unsorted hESC-CMs; (E) and (F): viability and $\Delta\psi_m$ for CD36$^+$ hESC-CMs; (G) and (H): viability and $\Delta\psi_m$ for CD36$^-$ hESC-CMs. The cells in the "Dox" groups were treated with 1 mM dox for 24 hrs; the cells in the "Dox+DRZ" groups were pre-treated with 200 mM DRZ for 1 hr, followed by co-treatment with 1 mM dox for 24 hrs. Cell viability and mitochondrial membrane potential $\Delta\psi_m$ were determined by the XTT and TMRE/MTG assays (n=7 and 9), respectively, and normalized to untreated hESC-CMs (i.e., the "Control" groups). *p<0.05, p<0.01, *p<0.001.
Figure 5D:
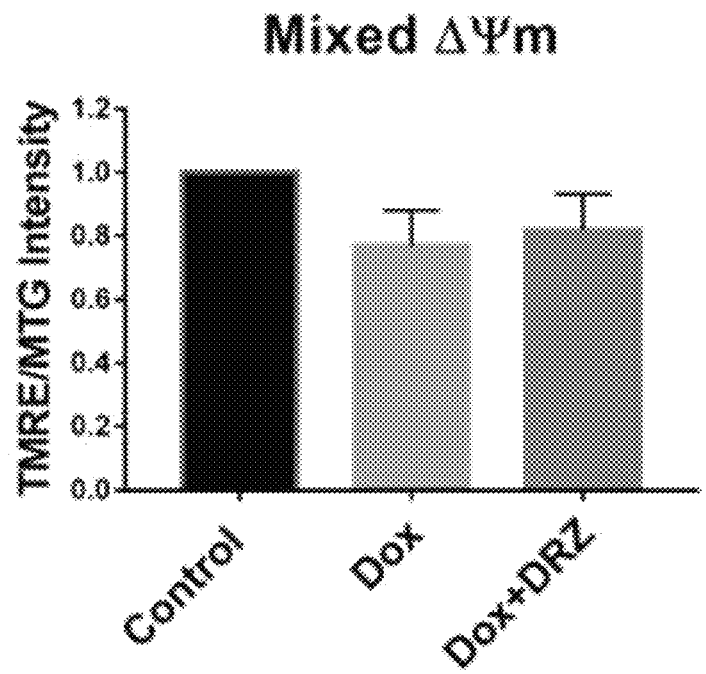
Figure 5E:
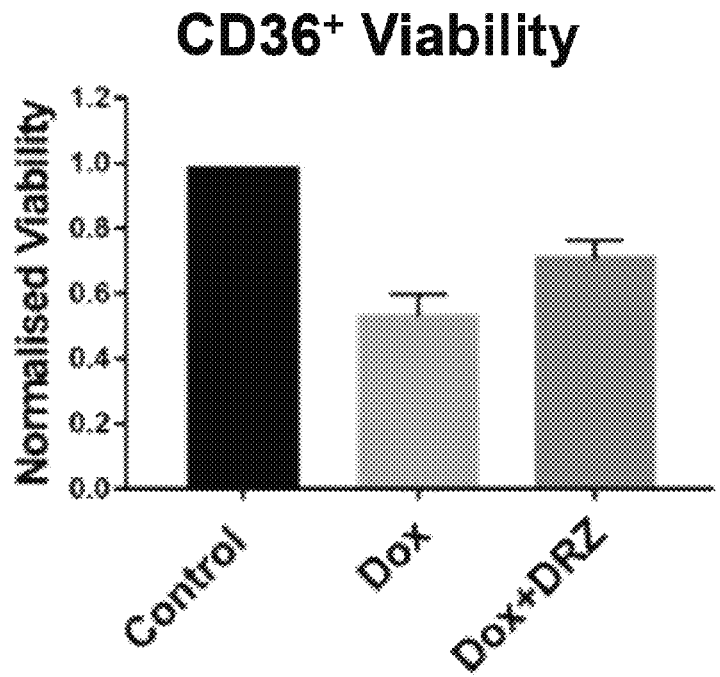
Figure 5F:
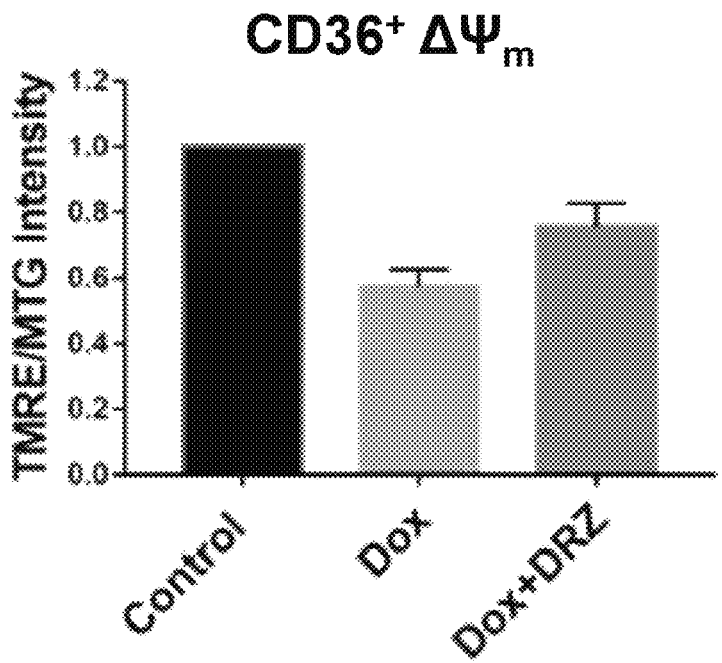
Figure 5G:
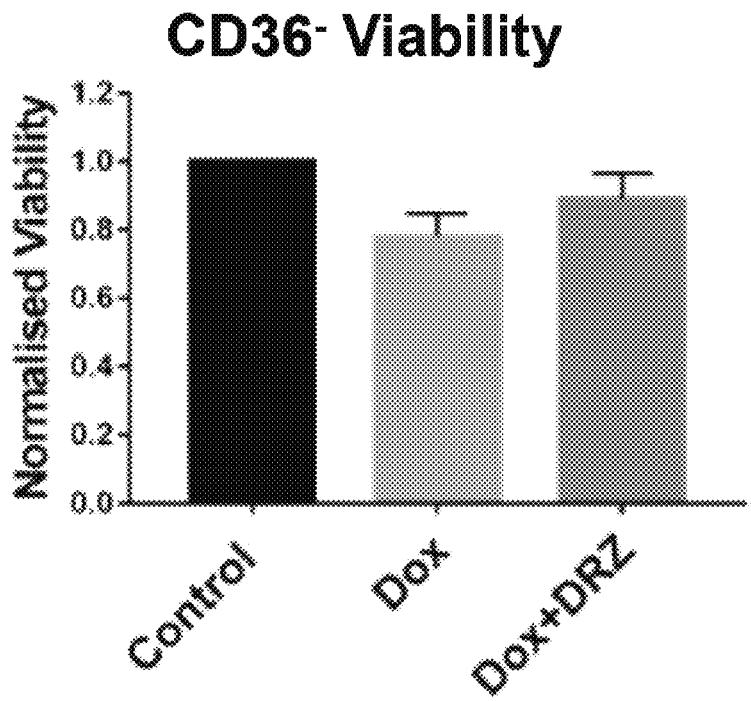
Figure 5H:
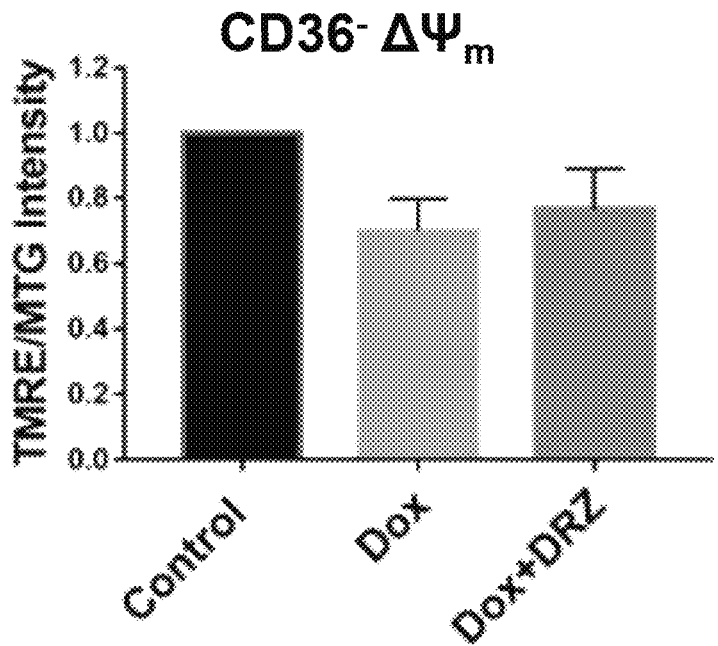
Figure 5I:
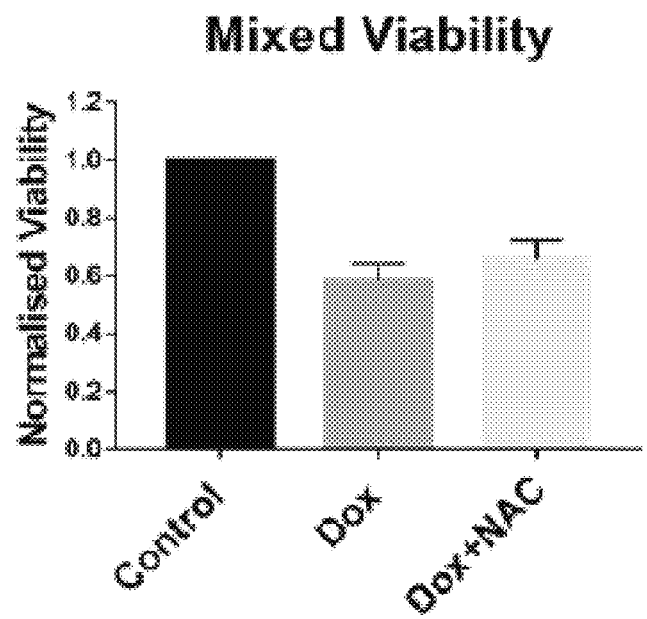
FIGS. 5I-5K are bar graphs showing the effect of N-acetylcysteine (NAC), a false active compound in reducing dox-induced cardiotoxicity, on the levels of cell viability of mixed (unsorted) hESC-CMs (I), CD36$^+$ hESC-CMs (J), and CD36$^-$ hESC-CMs (K) after exposure to dox. The cells in the "Dox" groups were treated with 1 mM dox for 24 hrs; the cells in the "Dox+NAC" groups were pre-treated with 1 mM NAC for 1 hr, followed by co-treatment with 1 mM dox for 24 hrs. Cell viability was determined by the XTT assay (n=4) and normalized to untreated cells (i.e., the "Control" groups).
Figure 5J:
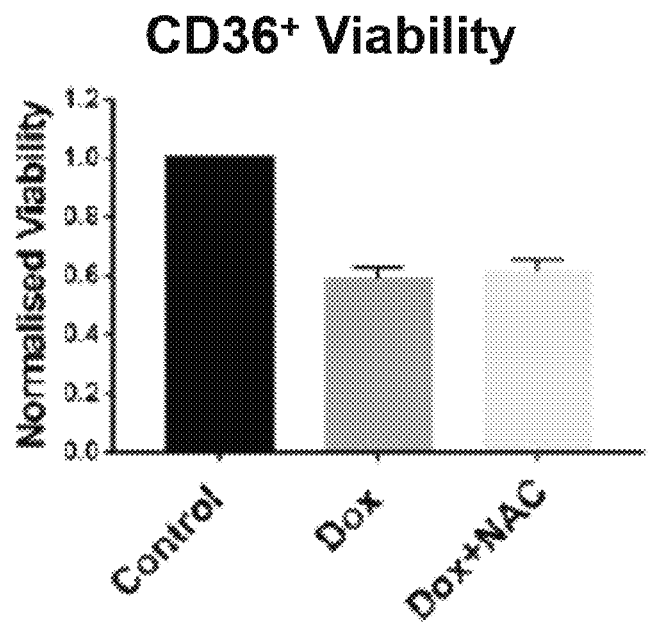
Figure 5K:
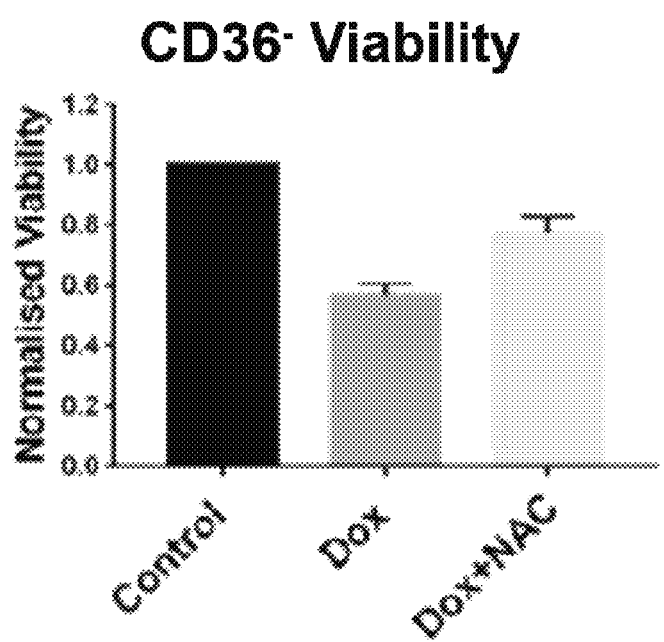

CD36$^+$ hPSCs are More Sensitive to Dox and Recapitulate Patient Responses to Dox-Treatment Mitochondria-rich CD36$^+$ hPSC-CMs can overcome the shortcomings of currently-used unsorted hPSC-CMs. Consistent with this, CD36$^+$ hESC-CMs have accelerated onset of dox-induced cell degeneration and showed a more severe decrease in cell viability and mitochondrial membrane potential ($\Delta\psi_m$) upon dox treatment compared to mixed (unsorted) or CD36$^-$ CMs (FIGS. 5A and 5B). CD36$^+$ hESC-CMs, but not mixed or CD36$^-$ CMs, responded to the protective effect of dexrazoxane against DCT (FIGS. 5C-5H). Conversely, N-acetylcysteine and vitamin E did not increase cell viability upon dox treatment (FIGS. 5I-K).

Parallel experiments were also performed using subpopulations of hiPSC-CMs instead of hESC-CMs. The aforedescribed results were confirmed with the subpopulations of hiPSC-CMs.

Therefore, the CD36$^+$ hPSC-CM model is a critical improvement over animal models, which failed to eliminate false positives (e.g., N-acetylcysteine), and existing hPSC-CM models, which failed to detect a true positive (dexrazoxane). With mature mitochondrial properties, CD36$^+$ hPSC-CMs is an ideal model to investigate the mechanisms of dox and evaluate treatment against its cardiotoxic effects.

We claim:
1. A subpopulation of mammalian stem cell- or mammalian progenitor cell-derived cardiomyocytes, wherein the subpopulation of cardiomyocytes are obtained from in vitro differentiation of a mammalian stem cell or a mammalian progenitor cell that results to cardiomyocytes having decreased interline variability and have identifiable mitochondrial maturation and identifiable sensitivity to oxidative stress, wherein the subpopulation of cardiomyocytes comprises a distinct portion of a population of mammalian stem cell- or mammalian progenitor cell-derived cardiomyocytes if selected and sorted, wherein the subpopulation of cardiomyocytes is,
   (i) a CD36$^+$ subpopulation, wherein when the selected distinct subpopulation is the CD36$^+$ subpopulation, the CD36$^+$ subpopulation has a higher proportion of cells expressing CD36 on the cell surface than the population of cardiomyocytes had, a higher average expression level of CD36 on the cell surface than the population of cardiomyocytes had, or a combination of both, or
   (ii) a CD36$^-$ subpopulation, wherein when the selected distinct subpopulation is the CD36$^-$ subpopulation, the CD36$^-$ subpopulation has a lower proportion of cells expressing CD36 on the cell surface than the population of cardiomyocytes had, a lower average expression level of CD36 on the cell surface than the population of cardiomyocytes had, or a combination of both.

2. The subpopulation of claim 1, wherein the subpopulation of cardiomyocytes was derived from the population of cardiomyocytes by selecting cells of the population that either (1) express CD36 on the cell surface or (2) do not express CD36 on the cell surface.

3. The subpopulation of claim 1, wherein the subpopulation of cardiomyocytes was derived from the population of cardiomyocytes by selecting cells of the population that either (1) express a relatively higher level of CD36 on the cell surface or (2) express a relatively lower level of CD36 on the cell surface.

4. The subpopulation of claim 1, wherein the population of cardiomyocytes was derived from human stem cells or human progenitor cells.

5. The subpopulation of claim 1, wherein the population of cardiomyocytes was derived from totipotent stem cells or pluripotent stem cells.

6. The subpopulation of claim 5, wherein the population of cardiomyocytes was derived from embryotic stem cells or induced pluripotent stem cells.

7. The subpopulation of claim 6, wherein the population of cardiomyocytes was derived from human embryotic stem cells Line H7 or H9.

8. The subpopulation of claim 6, wherein the population of cardiomyocytes was derived from MD1 human induced pluripotent stem cells.

9. The subpopulation of claim 1, wherein the subpopulation of cardiomyocytes is the $CD36^+$ subpopulation.

10. The subpopulation of claim 9, wherein the proportion of cells of the subpopulation of cardiomyocytes expressing CD36 on the cell surface is different than the proportion of cells of the population of cardiomyocytes expressing CD36 on the cell surface by a factor of between about 1.5 and about 10.

11. The subpopulation of claim 9, wherein the subpopulation of cardiomyocytes has a lower spontaneous beating frequency, a higher proportion of binucleated cells, higher expression of one or more sarcomeric proteins involved in cardiac maturation, higher expression of one or more ion channels involved in cardiac maturation, lower expression of one or more extracellular matrix proteins, lower expression of one or more cell adhesion proteins, higher expression of one or more genes involved in mitochondrial function, higher expression of one or more centromeric genes, higher expression of one or more genes associated with DNA repair, higher mitochondrial content, more polarized mitochondrial membrane potential, higher ATP production, higher cellular uptake of long-chain fatty acids, larger increase in mitochondrial membrane potential when fed with long-chain fatty acids, or combinations thereof, as compared to the $CD36^-$ subpopulation from the same population of cardiomyocytes.

12. The subpopulation of claim 11, further defined by one or more of the following features:
the one or more sarcomeric proteins involved in cardiac maturation comprise TNNI3, MYL2, or a combination thereof;
the one or more ion channels involved in cardiac maturation comprise KCNJ2;
the one or more extracellular matrix proteins comprise COL8A1;
the one or more cell adhesion proteins comprise NRP2;
the one or more genes involved in mitochondrial function comprise ATP5G4, ACADM, or a combination thereof;
the one or more centromeric genes comprises CENPH, CENPM, or a combination thereof; and
the one or more genes associated with DNA repair comprises EXO1, CDK1, or a combination thereof.

13. The subpopulation of claim 1, wherein the subpopulation of cardiomyocytes is the $CD36^-$ subpopulation.

14. The subpopulation of claim 13, wherein the proportion of cells of the subpopulation of cardiomyocytes not expressing CD36 on the cell surface is different than the proportion of cells of the population of cardiomyocytes not expressing CD36 on the cell surface by a factor of between about 1.5 and about 10.

15. The subpopulation of claim 13, wherein the subpopulation of cardiomyocytes has a higher spontaneous beating frequency, a lower proportion of binucleated cells, lower expression of one or more sarcomeric proteins involved in cardiac maturation, lower expression of one or more ion channels involved in cardiac maturation, higher expression of one or more extracellular matrix proteins, higher expression of one or more cell adhesion proteins, lower expression of one or more genes involved in mitochondrial function, lower expression of one or more centromeric genes, lower expression of one or more genes associated with DNA repair, lower mitochondrial content, less polarized mitochondrial membrane potential, lower ATP production, lower cellular uptake of long-chain fatty acids, smaller increase in mitochondrial membrane potential when fed with long-chain fatty acids, or combinations thereof, as compared to the $CD36^+$ subpopulation from the same population of cardiomyocytes.

16. The subpopulation of claim 1, wherein the cells of the subpopulation of cardiomyocytes express one or more markers associated with a cardiac phenotype, wherein the one or more markers are selected from CD172A, TNNT2, and a combination thereof.

17. The subpopulation of claim 1, wherein the subpopulation of cardiomyocytes is in media and isolated.

18. The subpopulation of claim 17, wherein subpopulation of cardiomyocytes is under conditions in which the cells exhibit (i) increased metabolism of fatty acids or (ii) increased tolerance for hypoxia.

19. The subpopulation of claim 17, wherein the media comprises fatty acids.

20. The subpopulation of claim 1, wherein the subpopulation of cardiomyocytes is attached to a cardiac tissue patch.

21. A method to isolate each of the subpopulation of cardiomyocytes of claim 1, comprising:
(a) culturing mammalian stem cell- or mammalian progenitor cell-derived cardiomyocytes for a time period sufficient for expression of CD36 on the cell surface of some of the cardiomyocytes;
(b) either:
(b1) isolating those of the cardiomyocytes (1) expressing CD36 on the cell surface or (2) not expressing CD36 on the cell surface to yield the subpopulation of cardiomyocytes, or
(b2) isolating those of the cardiomyocytes (1) expressing a relatively higher level of CD36 on the cell surface or (2) expressing a relatively lower level of CD36 on the cell surface to yield the subpopulation of cardiomyocytes.

22. The method of claim 21, wherein the time period in step (a) is between about 2 and about 150 days, between about 10 and about 120 days, between about 15 and about 90 days, or between about 30 and about 60 days.

23. The method of claim 21, wherein step (b1) comprises:
(i) contacting the cardiomyocytes from step (a) with a sorting agent that is specific for CD36 under conditions sufficient to allow binding of the sorting agent to CD36 on the cell surface of the cardiomyocytes; and
(ii) isolating those of the cardiomyocytes to which the sorting agent (1) has bound or (2) has not bound to yield the subpopulation of cardiomyocytes.

24. The method of claim 23, wherein the sorting agent comprises an antibody specific for CD36.

25. The method of claim 21, wherein step (b2) comprises:
(i) contacting the cardiomyocytes from step (a) with a sorting agent that is specific for CD36 under conditions sufficient to allow binding of the sorting agent to CD36 on the cell surface of the cardiomyocytes; and
(ii) isolating those of the cardiomyocytes to which the sorting agent (1) has bound at a relatively higher level or (2) has bound at a relatively lower level to yield the subpopulations of cardiomyocytes.

26. The method of claim 21, wherein in step (b) the subpopulation of cardiomyocytes is isolated using fluorescence-activated cell sorting or magnetic-activated cell sorting.

27. The method of claim 21, further comprising an additional step prior to step (b), wherein the additional step comprises sorting or separating cardiomyocytes from non-cardiomyocyte cells by isolating cells expressing CD127A on the cell surface.

28. A method to model a cardiac disease or disorder using at least one of the subpopulations of cardiomyocytes of claim 1, comprising:
(a) inducing the cardiac disease or disorder in the subpopulation of cardiomyocytes; and
(b) characterizing the cardiac disease or disorder in the subpopulation of cardiomyocytes from step (a).

29. The method of claim 28, wherein the cardiac disease or disorder is cardiac arrhythmia.

30. The method of claim 28, wherein the cardiac disease or disorder is induced by doxorubicin-induced cardiotoxicity, long QT syndrome, Brugada syndrome, genetic heart disease, amyloidosis, progeria, diabetic coma, jellyfish intoxication, hyperthyroidism, Yellow Fever, Chagas disease, aortic valve regurgitation, prescription drug abuse leading to arrhythmia, Rett syndrome, myocarditis, tricuspid atresia, Lyme disease, Churg-Strauss syndrome, forms of heart disease or failure involving arrhythmia, enlarged heart, broken heart syndrome, thyroid nodules, atrioventricular canal defect, cholera, mitral valve stenosis, multiple system atrophy (MSA), snoring, mitral valve prolapse, amniotic fluid embolism, gangrene, aplastic anemia, congenital heart disease in adults, heat exhaustion, Graves' disease, cardiomyopathy, premature ventricular contractions, Bradycardia, fatigue, tachycardia, dizziness or shortness of breath, diabetes, arrhythmogenic right ventricular cardiomyopathy, dilated or hypertrophic cardiomyopathies, or muscular dystrophies optionally selected from Duchenne and Becker muscular dystrophies and mitochondrial diseases.

31. The method of claim 28, wherein the subpopulation of cardiomyocytes is derived from induced pluripotent stem cells of a patient with the cardiac disease or disorder.

32. The method of claim 31, wherein step (a) is void.

33. A method to screen drugs or therapies for a cardiac disease or disorder using at least one of the subpopulations of cardiomyocytes of claim 1, comprising:
(a) inducing the cardiac disease or disorder in the subpopulations of cardiomyocytes;
(b) treating the subpopulations of cardiomyocytes from step (a) with an effective amount of one or more candidate compounds or therapies; and
(c) evaluating the efficacy of the candidate compound or therapy in reducing one or more symptoms of the cardiac disease or disorder.

34. A method to assess the cardiotoxic effect of a compound using at least one of the subpopulations of cardiomyocytes of claim 1, comprising:
(a) contacting the compound with the subpopulation of cardiomyocytes; and
(b) measuring the cardiotoxic effect of the compound on the subpopulation of cardiomyocytes.

35. A system that models a cardiac disease or disorder comprising at least one of the subpopulations of cardiomyocytes of claim 1.

36. The system of claim 35, wherein the cardiac disease or disorder is cardiac arrhythmia.

37. The system of claim 35, wherein the cardiac disease or disorder is induced by doxorubicin-induced cardiotoxicity, long QT syndrome, Brugada syndrome, genetic heart disease, amyloidosis, progeria, diabetic coma, jellyfish intoxication, hyperthyroidism, Yellow Fever, Chagas disease, aortic valve regurgitation, prescription drug abuse leading to arrhythmia, Rett syndrome, myocarditis, tricuspid atresia, Lyme disease, Churg-Strauss syndrome, forms of heart disease or failure involving arrhythmia, enlarged heart, broken heart syndrome, thyroid nodules, atrioventricular canal defect, cholera, mitral valve stenosis, multiple system atrophy (MSA), snoring, mitral valve prolapse, amniotic fluid embolism, gangrene, aplastic anemia, congenital heart disease in adults, heat exhaustion, Graves' disease, cardiomyopathy, premature ventricular contractions, Bradycardia, fatigue, tachycardia, dizziness or shortness of breath, diabetes, arrhythmogenic right ventricular cardiomyopathy, dilated or hypertrophic cardiomyopathies, or muscular dystrophies optionally selected from Duchenne and Becker muscular dystrophies and mitochondrial diseases.

* * * * *